United States Patent
Kaplan et al.

(10) Patent No.: US 9,554,989 B2
(45) Date of Patent: *Jan. 31, 2017

(54) SILK RESERVOIRS FOR DRUG DELIVERY

(71) Applicant: TRUSTEES OF TUFTS COLLEGE, Medford, MA (US)

(72) Inventors: David L. Kaplan, Concord, MA (US); Tuna Yucel, Medford, MA (US); Michael L. Lovett, Peabody, MA (US); Xiaoqin Wang, Winchester, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/386,545

(22) PCT Filed: Mar. 11, 2013

(86) PCT No.: PCT/US2013/030206
§ 371 (c)(1),
(2) Date: Sep. 19, 2014

(87) PCT Pub. No.: WO2013/142119
PCT Pub. Date: Sep. 26, 2013

(65) Prior Publication Data
US 2015/0045764 A1 Feb. 12, 2015

Related U.S. Application Data

(60) Provisional application No. 61/613,185, filed on Mar. 20, 2012.

(51) Int. Cl.
| | | |
|---|---|---|
| *A61K 9/00* | (2006.01) |
| *A61K 9/50* | (2006.01) |
| *A61K 31/00* | (2006.01) |
| *A61K 9/48* | (2006.01) |
| *A61K 31/13* | (2006.01) |
| *A61K 31/5415* | (2006.01) |

(52) U.S. Cl.
CPC ........... *A61K 9/0024* (2013.01); *A61K 9/0019* (2013.01); *A61K 9/0092* (2013.01); *A61K 9/4825* (2013.01); *A61K 9/5052* (2013.01); *A61K 31/00* (2013.01); *A61K 31/13* (2013.01); *A61K 31/5415* (2013.01)

(58) Field of Classification Search
CPC .... A61K 9/0024; A61K 9/0092; A61K 31/00; A61K 31/13; A61K 31/4196; A61K 31/4402; A61K 31/5415; A61K 47/42; A61K 9/0019; A61K 9/70
See application file for complete search history.

(56) References Cited

U.S. PATENT DOCUMENTS

| | | |
|---|---|---|
| 387,413 A | 8/1888 | Griffin et al. |
| 3,270,960 A | 9/1966 | Phillips |
| 3,773,919 A | 11/1973 | Boswell |
| 4,806,355 A | 2/1989 | Goosen et al. |
| 5,015,476 A | 5/1991 | Cochrum et al. |
| 5,093,489 A | 3/1992 | Diamantoglou |
| 5,263,992 A | 11/1993 | Guire |
| 5,270,419 A | 12/1993 | Domb |
| 5,538,735 A | 7/1996 | Ahn |
| 5,576,881 A | 11/1996 | Doerr et al. |
| 5,591,828 A | 1/1997 | Bosslet et al. |
| 5,902,800 A | 5/1999 | Green et al. |
| 6,127,143 A | 10/2000 | Gunasekaran |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 7,842,780 B2 | 11/2010 | Kaplan et al. |
| 8,178,656 B2 | 5/2012 | Kaplan et al. |
| 8,187,616 B2 | 5/2012 | Wang et al. |
| 2002/0028243 A1 | 3/2002 | Masters |
| 2003/0007991 A1 | 1/2003 | Masters |
| 2007/0212730 A1 | 9/2007 | Vepari et al. |
| 2008/0085272 A1 | 4/2008 | Kaplan et al. |
| 2009/0232963 A1 | 9/2009 | Kaplan et al. |
| 2009/0263430 A1 | 10/2009 | Scheibel et al. |
| 2009/0263460 A1 | 10/2009 | McDonald |

(Continued)

FOREIGN PATENT DOCUMENTS

| | | |
|---|---|---|
| WO | WO-93/11161 A1 | 6/1993 |
| WO | WO-2005/012606 A2 | 2/2005 |

(Continued)

OTHER PUBLICATIONS

Acharya, C. et al., Performance evaluation of a silk protein-based matrix for the enzymatic conversion of tyrosine to $_L$-DOPA, Biotechnol. J., 3:226-233 (2008).

Bayraktar, O. et al., Silk fibroin as a novel coating material for controlled release of theophylline, European Journal of Pharmaceutics and Biopharmaceutics, 60:373-381 (2005).

Beaucage, S. L. and Iyer, R. P., The Functionalization of Oligonucleotides Via Phosphoramidite Derivatives, Tetrahedron Report No. 329, 49(10):1925-1963 (1993).

Chothia, C. and Lesk, A. M., Canonical Structures for the Hypervariable Regions of Immunoglobulins, J. Mol. Biol. 196:901-917 (1987).

Demura, M and Asakura, T., Immobilization of Glucose Oxidase with Bombyx mori Silk Fibroin by Only Stretching Treatment and Its Application to Glucose Sensor, 33 Biotech Bioengin., 33:598 (1989).

(Continued)

*Primary Examiner* — Robert A Wax
*Assistant Examiner* — Olga V Tcherkasskaya
(74) *Attorney, Agent, or Firm* — Brenda Herschbach Jarrell; Brian E. Reese; Choate, Hall & Stewart LLP

(57) ABSTRACT

The present invention is directed to silk-based drug delivery compositions for controlled, sustained delivery of therapeutic agent(s) as well as methods of making and using the same.

13 Claims, 7 Drawing Sheets

(56) References Cited

U.S. PATENT DOCUMENTS

| | | |
|---|---|---|
| 2010/0028451 A1 | 2/2010 | Kaplan et al. |
| 2010/0178304 A1 | 7/2010 | Wang et al. |
| 2010/0279112 A1 | 11/2010 | Kaplan et al. |
| 2011/0171239 A1 | 7/2011 | Kaplan et al. |
| 2012/0052124 A1 | 3/2012 | Kaplan et al. |
| 2012/0070427 A1 | 3/2012 | Kaplan et al. |
| 2012/0076771 A1* | 3/2012 | Vepari .............. A61L 31/005 424/130.1 |
| 2012/0187591 A1 | 7/2012 | Wang et al. |
| 2013/0210726 A1 | 8/2013 | Franklin |
| 2014/0378661 A1* | 12/2014 | Lo ........................ D01F 1/10 530/353 |
| 2015/0202351 A1* | 7/2015 | Kaplan ............. A61B 5/0478 607/116 |

FOREIGN PATENT DOCUMENTS

| | | |
|---|---|---|
| WO | WO-2006/076711 A2 | 7/2006 |
| WO | WO-2008/150861 A1 | 12/2008 |
| WO | WO-2009/023615 A1 | 2/2009 |
| WO | WO-2009/126689 A2 | 10/2009 |
| WO | WO-2010/057142 A2 | 5/2010 |
| WO | WO-2011/005381 A2 | 1/2011 |
| WO | WO-2011/006133 A2 | 1/2011 |
| WO | WO-2011/011347 A2 | 1/2011 |
| WO | WO-2011/109691 A2 | 9/2011 |
| WO | WO-2012/145739 A1 | 10/2012 |

OTHER PUBLICATIONS

Eckstein, Fritz, Oligonucleotides and Analogues: A Practical Approach, Oxford University Press, 26 pages (1991).
Egholm, M. et al., Peptide Nucleic Acids (PNA). Oligonucleotide Analogues with an Achiral Peptide Backbone, J. Am. Chem. Soc. 114:1895-1897 (1992).
Egholm, M. et al., PNA hybridizes to complementary oligonucleotides obeying the Watson-Crick hydrogen-bonding rules, Nature, 365:566-568 (1993).
Elçin, Y. M. et al., Controlled Release of Endothelial Cell Growth Factor form Chitosan-Albumin Microspheres for Localized Angiogenesis: In Vitro and In Vivo Studies, Art. Cells, Blood Subs. and Immob. Biotech., 24(3):257-271 (1996).
Heath, Carole A., Cells for tissue engineering, TIBTECH 18:17-19 (2000).
Hersel, U. et al., RGD modified polymers: biomaterials for stimulated cell adhesion and beyond, Biomaterials 24:4385-4415 (2003).
Hoffman, S. et al., Silk fibroin as an organic polymer of controlled drug delivery, Journal of Controlled Release, 111:219-227 (2006).
Hollinger, P. et al., Diabodies: Small bivalent and bispecific antibody fragments, Proc. Natl. Acad. Sci., 90:6444-6448 (1993).
Hu, X. et al., Regulation of Silk Material Structure by Temperature-Controlled Water Vapor Annealing, Biomacromolecules 12:1686-1696 (2011).
International Preliminary Report on Patentability with Opinion, International Application No. PCT/US2013/030206, 9 pages (Oct. 2, 2014).
International Preliminary Report on Patentability, International Application No. PCT/US2013/033171, 11 pages, (Oct. 2, 2014).
Jin, H. et al., Water-Stable Silk Films with Reduced β-Sheet Content, Adv, Funct. Mater. 15:1241-1247 (2005).
Li, M. et al., Study on Porous Silk Fibroin Materials. II. Preparation and Characteristics of Spongy Porous Silk Fibroin Materials, J. Applied Polymer Science, 79:2192-2199 (2001).
Lovett, M. et al., Gel spinning of silk tubes for tissue engineering, Biomaterials, 29(35):4650-4657 (2008).
Lu, S. et al., Stabilization of Enzymes in Silk Films, Biomacromolecules 10:1032-1042 (2009).
Lucas, F. et al., The Silk Fibroins, Adv. Protein Chem., 13:107-242 (1958).
Meier, C. and Engels, J. W., Peptide Nucleic Acids (PNAs)—Unusual Properties of Nonionic Oligonucleotide Analogues, Angew. Chem. Int. Ed. Engl. 31(8):1008-1010 (1992).
Min, S. et al., Preparation and Characterization of Crosslinked Porous Silk Fibroin Gel, Transaction, 54(2):85-92 (1998).
Miyairi, S. and Sugiura, M., Properties of β-Glucosidase Immobilized in Sericin Membrane, J. Germent. Technol., 56(4):303-308 (1978).
Nazarov, R. et al., Porous 3-D Scaffolds from Regenerated Silk Fibroin, Biomacromolecules 5:718-726 (2004).
Pritchard, E. M. et al., Silk Fibroin Encapsulated Powder Reservoirs for Sustained Release of Adenosine, J. Control Release, 144(2):159-167 (2010).
Pritchard, E.M. and Kaplan, D.L., Silk fibroin biomaterials for controlled release drug delivery, Expert Opinion on Drug Delivery, 8(6):797-811 (2011).
Rosenberg, M. et al., Eds., The Pharmacology of Monoclonal Antibodies, Springer-Verlag Berlin Heidelberg, Chapter 11 (1994).
Schaffner, P. and Dard, M. M., Structure and function of RGD peptides involved in bone biology, Cell. Mol. Life Sci., 60:119-132 (2003).
Steller, K. E. and Letsinger, R. L., Effects of Distant Substituents on Photoinduced Aromatic Substitution Reactions, The Journal of Organic Chemistry, 35(2):308-313 (1970).
Takahashi, K. et al., Induction of Pluripotent Stem Cells form Adult Human Fibroblasts by Defined Factors, Cell 131:861-872 (2007).
Urquhart, J. et al., Rate-Controlled Delivery Systems in Drug and Hormone Research, Ann. Re. Pharmacol. Toxicol. 24:199-236 (1984).
Yu, J. et al., Induced Pluripotent Stem Cell Lines Derived from Human Somatic Cells, Science 318:1917-1920 (2007).
Zapata, G. et al., Engineering linear F(ab')$_2$fragments for efficient production in *Escherichia coli* and enhanced antiproliferative activity, Protein Engineering, 8(10):1057-1062 (1995).
Zarkoob, S., Structure and Morphology of Regenerated Silk Nano-Fibers Produced by Electrospinning, Dissertation, UMI Microform 9842114, 121 pages (1998).
Extended European Search Report for EP 13764579.2, 6 pages (Aug. 18, 2015).
International Search Report for PCT/US2013/030206, 4 pages (Jun. 21, 2013).
International Search Report for PCT/US2013/033171, 4 pages (Nov. 27, 2013).
Wang, X. et al., Silk microspheres for encapsulation and controlled release, Journal of Controlled Release, 117(3):360-370 (2007).
Written Opinion for PCT/US2013/030206, 7 pages (Jun. 21, 2013).
Written Opinion for PCT/US2013/033171, 9 pages (Nov. 27, 2013).

* cited by examiner

A. Temperature controller
B. Tube oven
C. Wire
D. Drill chuck
E. Bearing
F. Shaft
G. AC gear motor
H. Syringe pumps
I. Adjustable height stands
J. Slides

SILK RESERVOIRS FOR DRUG DELIVERY

CROSS-REFERENCE TO RELATED APPLICATIONS

This application claims benefit under 35 U.S.C. §119(e) of the U.S. Provisional Application No. 61/613,185, filed Mar. 20, 2012, the content of which is incorporated herein by reference in its entirety.

TECHNICAL FIELD

The present disclosure relates to silk compositions for sustained delivery of molecules, such as therapeutic agent(s), as well as methods of making and using the same. The disclosed compositions and methods can be used for administering therapeutic agents requiring repeat or frequent administration.

BACKGROUND

The effectiveness of therapeutic agents in general, is limited by patient compliance. At times, patient compliance is hindered by treatments that are inconvenient or cause patient discomfort. Importantly, certain therapeutic agents have deleterious effects if the plasma concentration thereof falls below a minimum concentration. Although some sustained release formulations are available which increase patient compliance, the majority employ poly(lactic-co-glycolic acid) (PLGA) which requires hazardous organic solvents and high temperature for processing thereof. Not only are such organic solvents environmentally undesirable but residual amounts thereof may be present in the end-product. Furthermore, hydrolytic degradation byproducts of PLGA polymers are acids, which may cause inflammation and degradation of the active ingredient. Thus, there is a need for improved pharmaceutical compositions lacking potentially inflammatory degradation byproducts that provide sustained delivery of therapeutic agent(s) which are manufactured in a manner that minimizes the use of hazardous organic solvents.

SUMMARY

The present disclosure provides silk-based drug delivery compositions that provide sustained delivery of therapeutic agent(s). In addition to fostering patient compliance, such silk-based drug delivery composition exhibit excellent biocompatibility and non-inflammatory degradation products, such as peptides and amino acids. Therefore, potential use of silk in sustained release pharmaceutical formulations as a carrier could minimize immune response, and enhance stability of an active ingredient as compared to other polymeric formulations with acidic degradation byproducts (e.g., PLGA). Silk compositions can be processed in completely aqueous based solvents. Accordingly, such silk-based drug delivery compositions avoid the use of hazardous organic solvents that are used in the preparation of PLGA based sustained release formulations. Generally, the silk-based drug delivery composition described herein comprises a therapeutic agent encapsulated in a substantially silk reservoir implant or silk injectable reservoir comprising silk fibroin, wherein the ends of the silk reservoir implant or silk injectable reservoir are closed to form a silk reservoir implant or silk injectable reservoir. Further, the silk-based drug delivery composition is capable of sustained delivery of the therapeutic agent in vivo.

In one aspect, the present disclosure provides a method for preparing a silk-based drug delivery composition for delivery of a therapeutic agent. The method comprises forming a silk tube from silk fibroin, loading the silk tube with a therapeutic agent, closing the silk tube ends such that the therapeutic agent is sealed therein. The closed tube ends can be coated with a polymer solution, such as a silk solution to form a silk reservoir implant or silk injectable reservoir.

Without limitaitons, any method known to one of skill in the art can be used to form the silk tube. In some embodiments, the silk tube for the silk reservoir implant or silk injectable reservoir is made by gel-spinning. In gel-spinning, a silk fibroin solution is delivered over a rotating mandrel which is simultaneously reciprocated horizontally. The silk fibroin forms a coating on the mandrel. This process can be repeated as many times as needed to obtain a desired number of coating layers or wall thickness for the silk reservoir implant or silk injectable reservoir.

In some embodiments, the silk tube for the silk reservoir implant or silk injectable reservoir is made by a novel and non-obvious modification of the gel-spinning technique termed filk-spinning herein. In film-spinning, a silk fibroin solution is delivered over a rotating mandrel which is simultaneously reciprocated horizontally. The silk fibroin forms a coating on the mandrel and the silk coating is treated with heat while the mandrel is spinning. This process can be repeated as many times as needed to obtain a desired number of coating layers or wall thickness for the silk reservoir implant or silk injectable reservoir.

In some embodiments, the silk tube for the silk reservoir implant or silk injectable reservoir is made dip-coating. In dip-coating a rod of a selected diameter is contacted with, i.e., dipped into a solution of silk fibroin, thereby forming a coating on the rod. The coating is then dried and removed from the rod, whereby a tube of tubukar composition comprising the silk fibroin is prepared. The coating process can be repeated as many times as needed to obtain a desired number of coating layers of wall thickness for the silk reservoir implant or silk injectable reservoir.

Provided herein is also a silk-based drug delivery composition prepared using the aforementioned methods.

In another aspect, provided herein is a pharmaceutical composition. The pharmaceutical composition comprises a silk-based drug delivery composition described herein and a pharmaceutically acceptable excipient.

The disclosure also provides kits comprising a silk-based drug delivery composition and instructions for use.

In yet another aspect, provided herein is a method for sustained delivery in vivo of a therapeutic agent. The method comprises administering a silk-based drug delivery composition described herein to a subject. For administering to a patient, the silk-based drug delivery composition can be formulated with a pharmaceutically acceptable excipient or carrier. The therapeutic agent can be delivered in a therapeutically effective amount over a period of time.

In still another aspect, provided herein is a method for treating schizophrenia or a bipolar disorder in a subject. The method comprises administering a silk-based drug delivery composition described herein to a subject in need thereof. For treatment of schizophrenia or a bipolar disorder, the therapeutic agent can be 2-[4-[3-[2-(trifluoromethyl)-10H-phenothiazin-10-yl]propyl]piperazin-1-yl]ethanol (fluphenazine). Fluphenazine can be delivered in a therapeutically effective amount over a period of time.

In yet still another embodiment, provided herein is a method for treating Alzheimer's disease in a subject. The method comprises administering a silk-based drug delivery composition described herein to a subject in need thereof. For treatment of Alzheimer's disease, the therapeutic agent can be 3,5-dimethyltricyclo[3.3.1.1$^{3,7}$]decan-1-amine (3,5-dimethyladamantan-1-amine, or memantine). Memantine can be delivered in a therapeutically effective amount over a period of time.

In yet another aspect, provided herein is a method for preparing a silk reservoir implant or silk injectable reservoir, from silk fibroin. The method comprises delivering silk fibroin solution over a mandrel, which is simultaneously reciprocated horizontally while being rotated along its axis to form a silk coating thereon. The silk coating is treated with heat while the mandrel is rotating to form a silk film. Optionally, the delivery and heat treatment steps can be repeated as many times as needed to obtain desired number of coating layers, wall thickness, or other desired property. When more than one coating is applied, thickness of all coatings can be the same, all different, or any combinations thereof. Further, thickness of two neighboring coatings can be the same or different.

DETAILED DESCRIPTION

Figure 1:
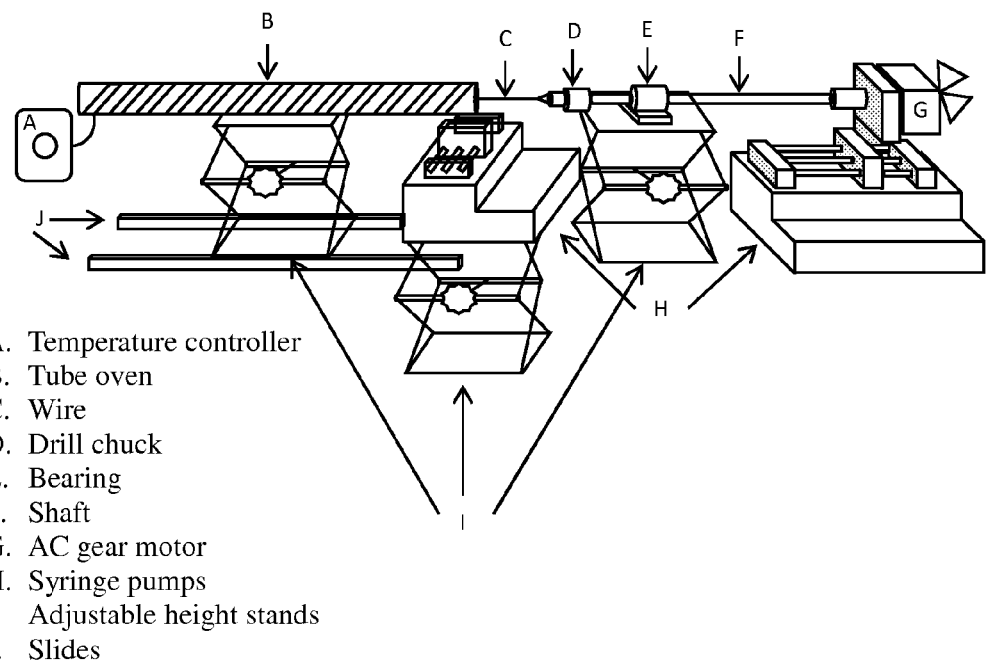
FIG. 1 illustrates a schematic of the film-spinning set-up employed for preparing film-spun silk tubes of the present disclosure. In particular, "A" refers to a temperature controller; "B" refers to a tube oven; "C" refers to a wire; "D" refers to a drill chuck; "E" refers to a bearing; "F" refers to a shaft; "G" refers to a AC gear motor; "H" refers to syringe pumps; "I" refers to adjustable height stands; and "J" refers to slides.

In one aspect, described herein is a silk-based drug delivery composition and method for preparing the same. The silk-based drug delivery composition comprises a therapeutic agent encapsulated in a silk-fibroin based tube comprising silk fibroin, wherein the ends of the silk tube are closed/sealed to form a silk reservoir implant or silk injectable reservoir. The drug delivery composition allows for the controlled or sustained release of therapeutic agents in vivo.

One of skill in the art would recognize that the in some embodiments, the drug delivery composition, i.e., the silk-fibroin-based tube with the closed ends, can be considered a capsule like composition, wherein the capsule is made from silk-fibroin and the at least a part of the amount of the therapeutic agent is present in the lumen of the film-spun silk tube. Accordingly, in some embodiments, at least 5%, (e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98%) of the therapeutic agent is present in the lumen of the film-spun silk tube. In some embodiments, the entire amount of the therapeutic agent is present in the lumen of the drug delivery composition. Without limitations the silk reservoir implant or silk injectable reservoir can have a cross-section. For example, cross-section of the silk reservoir implant or silk injectable reservoir can be, for example without limitation, round, substantially round, oval, substantially oval, elliptical, substantially elliptical, triangular, substantially triangular, square, substantially square, hexagonal, substantially hexagonal, or the like. In some embodiments, at least a part of the amount of therapeutic agent is present in the wall of the silk reservoir implant or silk injectable reservoir.

In some embodiments, a second therapeutic agent can be dispersed within the wall of silk reservoir implant or silk injectable reservoir. The second therapeutic agent can be present in any form suitable for a particular method to be used for encapsulation and/or dispersion. For example, the second therapeutic agent can be in the form of a solid, liquid, or gel. In some embodiments, the therapeutic agent can be in the form of a powder or a pellet. In some embodiments, the therapeutic agent can be dispersed or encapsulated in a silk solution before forming the silk tube. In some embodiments, the therapeutic agent can be dispersed or encapsulated in a silk solution or silk tube after forming the silk tube. For example, the therapeutic agent can be dispersed homogeneously or heterogeneously within the silk tube wall, e.g., by pre-loading or post-loading silk fibroin solution, e.g., as described in the U.S. Provisional Application No. 61/545, 786, the International Application No. WO/2011/109691, and U.S. Pat. No. 8,178,656, or dispersed in a gradient, e.g., using the carbodiimide-mediated modification method described in the U.S. Patent Application No. US 2007/0212730. In some embodiments, the second therapeutic agent can be coated on a surface of the silk tube wall, e.g., via diazonium coupling reaction (see, e.g., U.S. Patent Application No. US 2009/0232963), and/or avidin-biotin interaction (see, e.g., International Application No.: WO 2011/011347). In some embodiments, the second therapeutic agent can be encapsulated in the silk tube wall, e.g., by blending the therapeutic agent into a silk solution before processing into the silk tube. See, e.g., U.S. Pat. No. 8,187,616; and U.S. Pat. App. Nos. US 2008/0085272, US 2010/0028451, US 2012/0052124, US 2012/0070427, and US 2012/0187591, the contents of which are incorporated herein by reference. In some embodiments, the therapeutic agent can be present in a form of a fusion protein with silk protein, e.g., by genetically engineering silk to generate a fusion protein comprising the therapeutic agent.

Generally, the silk reservoir implant or silk injectable reservoir can have any length desired. For example, length of the silk reservoir implant or silk injectable reservoir can be from about 1 mm to about 10 cm. In some embodiments, length of the silk reservoir implant or silk injectable reservoir can be from about 1 mm to about 5 cm.

Without wishing to be bound by a theory, it is believed that the wall thickness of the silk reservoir implant or silk injectable reservoir can affect the release rate of the therapeutic agent encapsulated in the silk reservoir implant or silk injectable reservoir. Accordingly, the silk reservoir implant or silk injectable reservoir can be selected to have a wall thickness that provides a desired rate of release. For example, wall thickness can range from about 50 µm to about 5 mm. In some embodiments, the wall thickness can be from about 50 µm to about 500 µm, from about 50 µm to about 1,000 µm, from about 200 µm to about 300 µm, from about 600 µm to about 800 µm, from about 200 µm to about 800 µm, from about 300 µm to about 700 µm, from about 400 µm to about 600 µm, or about 500 µm. In some embodiments, the wall thickness can be greater than about 1,000 µm. In some embodiments, the wall thickness can be less than about 100 µm. In some embodiments, the wall thickness can be about 0.25 mm, about 0.5 mm, about 0.75 mm, about 0.9 mm, about 1.0 mm, or about 1.7 mm.

The silk reservoir implant or silk injectable reservoir can have a lumen extending therethrough. The lumen can have the same cross-section as that of the silk reservoir implant or silk injectable reservoir or a cross-section that is different than that of the silk reservoir implant or silk injectable reservoir. For example, the cross-section of the lumen can be round, substantially round, oval, substantially oval, elliptical, substantially elliptical, triangular, substantially triangular, square, substantially square, hexagonal, substantially hexagonal, or the like.

In some embodiments, the lumen has a diameter. The diameter can be approximately the same as the diameter of the rotating mandrel used in the preparation of the silk reservoir implant or silk injectable reservoir. It is understood that the diameter can vary along the length of the lumen. Without limitations, the diameter can be from about 100 nm to about 10 mm. In some embodiments, the diameter can be from about 1 mm to about 5 mm, from about 1 mm to about 3 mm, from about 3 mm to about 5 mm, from about 2 mm to about 4 mm, about 1 mm, about 2 mm, about 3 mm, about 4 mm, or about 5 mm. In some embodiments, the diameter can be greater than about 5 mm. In some embodiments, the diameter can be less than about 1 mm. In so silk reservoir implant or silk injectable reservoir me other embodiments, the diameter of less than about 20 mm, for example, less than about 10 mm, or less than about 5 mm.

Generally, any amount of the therapeutic agent can be loaded into the silk reservoir implant or silk injectable reservoir to provide a desired amount release over a period of time. For example, from about 0.1 mg to about 1000 mg of the therapeutic agent can be loaded in a silk reservoir implant or silk injectable reservoir. In some embodiment, amount of therapeutic agent in composition, is selected from the range about from 0.001% (w/w) up to 95% (w/w), preferably, from about 5% (w/w) to about 75% (w/w), and, most preferably, from about 10% (w/w) to about 60% (w/w).

In some embodiments, amount of the therapeutic agent in the silk-based drug delivery composition is more than the amount recommended for one dosage of the therapeutic agent. For example, if the recommended dosage of the therapeutic agent is X amount then the silk-based drug delivery composition can comprise an amount which is 1.25, 1.5, 1.75, 2, 2.5, 3, 4, 5, 6, 7, 8, 9, 10 or more times higher than X amount. Without wishing to be bound by a theory, this can allow administering the therapeutic agent to obtain a therapeutic effect which is similar to one obtained with multiple administration of the therapeutic agent administered without the silk-based drug delivery composition. As used herein, the term "therapeutic effect" refers to a consequence of treatment, the results of which are judged to be desirable and beneficial.

The inventors have also discovered that the silk-based drug delivery composition can also increase duration of the therapeutic effect for the therapeutic agent. Accordingly, the silk-based drug delivery composition can comprise the therapeutic agent in an amount, which is less than the amount recommended for one dosage of the therapeutic agent. For example, if the recommended dosage of the therapeutic agent is X amount then the silk-based drug delivery composition can comprise an amount which is X/2, X/3, X/4, X/5, X/6, X/7, X/8, X/9, X/10 or less. Without wishing to be bound by a theory, this can allow administering a lower dosage of the therapeutic agent to obtain a therapeutic effect, which is similar to a higher dosage administered without the silk-based drug delivery composition.

In some embodiments, amount of the therapeutic agent in the silk-based drug delivery composition is equal to the amount recommended for one dosage of the therapeutic agent. For example, if the recommended dosage of the therapeutic agent is X amount, then the silk-based drug delivery composition comprises X amount of the therapeutic agent. Without wishing to be bound by a theory, this can allow less frequent administration of the therapeutic agent to obtain a therapeutic effect over a longer period of time.

As used herein, the term "sustained delivery" is refers to continual delivery of a therapeutic agent in vivo or in vitro over a period of time following administration. For example, sustained release can occur over a period of at least several days, a week or several weeks. Sustained delivery of the agent in vivo can be demonstrated by, for example, the continued therapeutic effect of the agent over time. Alternatively, sustained delivery of the agent may be demonstrated by detecting the presence of the agent in vivo over time. In some embodiments, the sustain release is over a period of one week, two weeks, three weeks, four weeks, one month, two months, three months, four months, five months, six months or longer. As described above, wall thickness can affect the release rate of the therapeutic agent encapsulated in the silk reservoir implant or silk injectable reservoir.

The silk-based drug delivery composition can provide or release an amount of the therapeutic agent, which provides a therapeutic effect similar to as provided by a recommended dosage of the therapeutic agent for the same period of time. For example, if the recommended dosage for the therapeutic agent is once daily, then the silk-based drug delivery composition releases that amount of therapeutic agent, which is sufficient to provide a similar therapeutic effect as provided by the once daily dosage.

Daily release of the therapeutic agent can range from about 1 ng/day to about 1000 mg/day. For example, amount released can be in a range with a lower limit of from 1 to 1000 (e.g., every integer from 1 to 1000) and upper limit of from 1 to 1000 (e.g. every integer from 1 to 1000), wherein the lower and upper limit units can be selected independently from ng/day, µg/day, mg/day, or any combinations thereof.

In some embodiments, daily release can be from about 1 µg/day to about 10 mg/day, from about 0.25 µg/day to about 2.5 mg/day, or from about 0.5 µg/day to about 5 mg/day. In some embodiments, daily release of the therapeutic agent can range from about 100 ng/day to 1 mg/day, for example, or about 500 ng/day to 5 mg/day, or about 100 µg/day.

The inventors have discovered that release of the therapeutic agent from the silk reservoir implant or silk injectable reservoir composition follows near zero-order release kinetics over a period of time. For example, near zero-order release kinetics can be achieved over a period of one week, two weeks, three weeks, four weeks, one month, two months, three months, four months, five months, six months, twelve months, one year or longer.

Further, no significant apparent initial burst release is observed from the drug delivery composition described herein. Accordingly, in some embodiments, the initial burst of the therapeutic agent within the first 48, 24, 18, 12, or 6 hours of administration is less than 25%, less than 20%, less than 15%, less than 10%, less than 9%, less than 8%, less than 7%, less than 6%, less than 5%, less than 4%, less than 3%, less than 2%, or less than 1% of the total amount of therapeutic agent loaded in the drug delivery composition. In some embodiments, there is no initial burst of therapeutic agent within the first 6 or 12 hours, 1, 2, 3, 4, 5, 6, 7 days, 1 and 2 weeks of administration.

Additionally, the silk-based drug delivery composition can also comprise a targeting ligand. As used herein, the term "targeting ligand" refers to any material or substance which can promote targeting of the drug delivery composition to tissues and/or receptors in vivo and/or in vitro. The targeting ligand can be synthetic, semi-synthetic, or naturally-occurring. Materials or substances which can serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present disclosure include cell adhesion molecules (CAM), among which are, for example, cytokines, integrins, cadherins, immunoglobulins and selectin. The silk drug delivery composition can also encompass precursor targeting ligands. A precursor to a targeting ligand refers to any material or substance which can be converted to a targeting ligand. Such conversion can involve, for example, anchoring a precursor to a targeting ligand. Exemplary targeting precursor moieties include maleimide groups, disulfide groups, such as ortho-pyridyl disulfide, vinylsulfone groups, azide groups, and [agr]-iodo acetyl groups.

The targeting ligand can be covalently (e.g., cross-linked) or non-covalently linked to the silk-based drug delivery composition. For example, a targeting ligand can be covalently linked to silk fibroin used for making the silk reservoir implant or silk injectable reservoir or for coating the film-spun silk tube ends. Alternatively or in addition, a targeting ligand can be linked to an additive present in the silk fibroin solution which is used for making the silk reservoir implant or silk injectable reservoir or for coating the film-spun silk tube ends.

In addition, without wishing to be bound by a theory, encapsulating the therapeutic agent in a silk reservoir implant or silk injectable reservoir can increase the in vivo half-life of the therapeutic agent. For example, in vivo half-life of an encapsulated therapeutic agent can increase by at least 5%, at least 10%, at least 15%, at least 20%, at least 30%, at least 40%, at least 50%, at least 60%, at least 90%, at least 1-fold, at least 1.5-folds relative to the non-encapsulated therapeutic agent.

Again not wishing to be bound by a theory, encapsulating a therapeutic agent in a silk reservoir implant or silk injectable reservoir can increase the duration of effect for the therapeutic agent. For example, amount of therapeutic agent encapsulated in the silk-based drug delivery composition provides a therapeutic effect for a period of time, which is longer than when the same amount of therapeutic agent is administered without the silk-based drug delivery composition. In some embodiments, duration of therapeutic effect is at least one day, at least two days, at least three days, at least four days, at least five days, at least six days, at least seven days, at least one week, at least two weeks, at least three weeks, at least four weeks, at least one month, at least two months, at least three months, at least four months, at least five months, at least six months or longer than the duration of effect when the therapeutic agent is administered without the silk-based drug delivery composition.

The silk-based drug delivery composition can also stabilize the bioactivity of a therapeutic agent under a certain condition, e.g., under an in vivo physiological condition. See, for example, WO 2012/145739, content of which is incorporated herein by reference in its entirety, for additional details on compositions and methods of stabilization of active agents. Accordingly, the silk-based drug delivery composition can increase the in vivo half-life of the therapeutic agent. For example, in vivo half-life of a therapeutic agent in a silk-based drug delivery composition described herein can be increased by at least about 5%, at least about 10%, at least about 15%, at least about 20%, at least about 30%, at least about 40%, at least about 50%, at least about 60%, at least about 90%, at least about 1-fold, at least about 1.5-folds relative to the therapeutic agent present in a non-silk matrix. Without wishing to be bound by theory, the silk-based drug delivery composition can provide a longer therapeutic effect. Stated another way, an increase in in vivo half-life of a therapeutic agent can allow loading of a smaller amount of the therapeutic agent for the same duration of therapeutic effect.

Furthermore, the silk-based drug delivery composition can increase bioavailability of the encapsulated therapeutic agent. As used herein, the term 'bioavailability' refers to the amount of a substance available at a given site of physiological activity after administration. Bioavailability of a given substance is affected by a number of factors including but not limited to degradation and absorption of that substance. Administered substances are subject to excretion prior to complete absorption, thereby decreasing bioavailability.

In some embodiments, bioavailability of an encapsulated therapeutic agent can increase by at least 5%, at least 10%, at least 15%, at least 20%, at least 25%, at least 30%, at least 35%, at least 40%, at least 50%, at least 60%, at least 70%, at least 80%, at least 90%, at least 1-fold, at least 1.5-fold, at least 2-fold, at least 5-fold, at least 5-fold, at least 10-fold or more relative to the non-encapsulated therapeutic agent.

Method for Preparation of Silk Tubes

In another aspect, described herein is a method for preparing a silk reservoir implant or silk injectable reservoir, wherein the silk reservoir implant or silk injectable reservoir comprises silk fibroin. The method comprises forming a tube from silk fibroin, loading the silk tube with a therapeutic agent, closing the silk tube such that the therapeutic agent is sealed therein, and coating the closed ends of the silk tube with a silk fibroin solution to form a silk reservoir implant or silk injectable reservoir.

Generally, silk tubes can be made using any method known in the art. For example, tubes can be made using molding, dipping, electrospinning, gel spinning, and the like. Gel spinning involves winding an aqueous solution of silk around a reciprocating rotating mandrel. Final gel-spun silk tube porosity, structure and mechanical properties could be controlled via different post-spinning processes such as alcohol (e.g., methanol, ethanol, etc. . . . ) treatment, air-drying, water annealing, or lyophilization. In gel-spinning, a silk fibroin solution is delivered over a rotating mandrel which is simultaneously reciprocated horizontally. The silk fibroin forms a coating on the mandrel. This process can be repeated as many times as needed to obtain a desired number of coating layers or wall thickness for the silk reservoir implant or silk injectable reservoir. Gel spinning is described in Lovett et al. (*Biomaterials,* 29(35):4650-4657 (2008)) and the construction of gel-spun silk tubes is described in PCT application no. PCT/US2009/039870, filed Apr. 8, 2009, content of both of which is incorporated herein by reference in their entirety. In dip-coating a rod of a selected diameter is contacted with or dipped into a solution of silk fibroin, thereby forming a coating on the rod. The coating is then dried and removed from the rod, whereby a tube of comprising the silk fibroin is prepared. The coating and drying process can be repeated as many times as needed to obtain a desired number of coating layers of wall thickness for the silk reservoir implant or silk injectable reservoir. Construction of silk tubes using the dip-coating method is described in PCT application no. PCT/US2008/072742, filed Aug. 11, 2008, content of which is incorporated herein by reference in its entirety. Without wishing to be bound by a theory, it is believed that the inner and outer diameter of the silk tube can be controlled more readily using gel-spinning than dip-coating technique.

Accordingly, described herein is a method for preparation of a film-spun silk tube. The method is based on a novel and non-obvious modification of the gel spinning technique as described in PCT application no. PCT/US2009/039870 and the novel and non-obvious dip-coating technique as described in PCT application no. PCT/US2008/072742, content of both of which is incorporated herein by reference in their entirety. Accordingly, the film-spun silk tube preparation method described herein is different from that described in PCT/US2009/039870. The inventors have discovered inter alia that heating the silk during gel-spinning surprisingly, unexpectedly provides a silk tube with a controlled morphology. Accordingly, the tube preparation technique described herein is termed "film spinning," as it involves a heat treatment step using an in-line heating element to transition the silk spinning solution into a tubular film with controlled morphology. Additionally, the film-spinning method described herein employs a syringe pump to control the flow rate of an injected silk spinning solution precisely. Precise control over the injection rate is an important difference with the gel spinning technique and provides a more controlled tube wall thickness for applications involving controlled delivery of therapeutic agent(s). In some embodiments, the set-up depicted in FIG. 1 can be employed for film spinning silk tubes.

Generally, the film spinning method for forming a silk tube comprises: (i) delivering a silk fibroin solution onto a mandrel which is reciprocated horizontally while being rotated along its longitudinal axis to form a silk coating thereon and heating the silk coating while the mandrel is rotating to form a silk film on the rotating mandrel. The mandrel can have an elongated structure with a longitudinal axis. The inventors have discovered that simultaneous rotation of the mandrel and treatment of film with heat unexpectedly results in coating thickness uniformity.

Without limitations, the delivering and heating steps can be repeated one or more times (e.g., 1, 2, 3, 4, 5, 6, 7, 8, 9, 10 or more) to form one or more coatings of the silk film. In some embodiments, the delivering and heating steps are repeated at least 5, at least 10, at least 50, at least 100, at least 250, at least 500, at least 1000, at least 5000, at least 10000 or more times. In some embodiments, the delivering and heating steps are repeated until a desired wall thickness for the film-spun silk tube is obtained.

The mandrel can be made of any material known to one of skill in the art. For example, mandrel can be made of stainless steel or a stainless steel mandrel coated with a synthetic fluoropolymer.

The mandrel can have a rotational speed of about 0 to about 1000 rpm and an axial movement speed of about 0 to about 1000 mm/s.

The silk fibroin solution can be delivered onto the mandrel using any method known in the art. For example, the silk fibroin solution can be applied using an applicator. In some embodiments, the applicator can be a syringe containing the supply of the silk solution.

The silk fibroin solution can be delivered onto the mandrel using a needle. A needle of any gauge can be used for delivery. For example, the needle can be of at least 21 gauge. In some embodiment, needle is of gauge from about 25 to about 30.

Without limitations, the silk fibroin solution can be delivered onto the mandrel at any flow rate. For example, a 30 wt % silk solution can be delivered at a flow rate of 0.02 mL/min to dispense approx. 1 μL of silk solution per millimeter of axial displacement of a 2.7 mm diameter wire rotating at a speed of 70 rpm.

The silk coating can be heated simultaneously while the silk fibroin solution is being delivered onto the mandrel or after delivery has finished. For example, the silk coating can be treated with heat within 5 seconds, within 10 second, within 14 second, within 25 seconds, within 30 seconds, within 35 second, within 40 seconds, within 45 seconds, within 50 seconds, within 55 seconds, within 1 minute, within 2 minutes, within 3 minutes, within 4 minutes, within 5 minutes, within 6 minutes, within 7 minutes, within 8 minutes, within 9 minutes, within 10 minutes, within 15 minutes, within 20 minutes, within 25 minutes, within 30 minutes, within 45 minutes, within 1 hour, within 2 hours, or within 3 hours, within 6 hours of delivery of the silk solution onto the mandrel.

Any temperature higher than room temperature can be used for heat treating the silk film on the support structure. For example, temperature for the heat treatment can range from about 30° C. to about 90° C. In some embodiments, temperature for the heat treatment can range from about 35° C. to about 80° C., from about 40° C. to about 75° C., from about 50° C. to about 70° C., or from about 55° C. to about 65° C. In some embodiments, temperature for the heat treatment is 67±3° C., or 47±3° C.

Further, the silk film on the support structure can be heat treated any period of time. For example, heat treatment can be for a period of about 1 minute to about 6 hours. In some embodiments, heat treatment can be for from about 10 minutes to about 300 minutes. In some embodiments, heat treatment can be for about 1, 2, 3, 4, 5, 10, 20, 30, or 60 minutes. In some embodiments, heat treatment can be for duration of the spinning process.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use according to the present disclosure can be obtained from a solution containing a genetically engineered silk, such as from bacteria, yeast, mammalian cells, transgenic animals or transgenic plants. See, for example, WO 97/08315 and U.S. Pat. No. 5,245,012, content of both of which is incorporated herein by reference.

The silk fibroin solution can be prepared by any conventional method known to one skilled in the art. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt is consequently removed using, for example, dialysis or chromatography.

If necessary, the solution can then be concentrated using, for example, dialysis against a hygroscopic polymer, for example, PEG, a polyethylene oxide, amylose or sericin. Preferably, the PEG is of a molecular weight of 8,000-10,000 g/mol and has a concentration of 10-50%. A slide-a-lyzer dialysis cassette (Pierce, MW CO 3500) is preferably used. However, any dialysis system may be used. The dialysis is for a time period sufficient to result in a final concentration of aqueous silk solution between 10-30%. In most cases dialysis for 2-12 hours is sufficient. See, for example, PCT application PCT/US/04/11199, content of which is incorporated herein by reference.

Alternatively, the silk fibroin solution can be produced using organic solvents. Such methods have been described, for example, in Li, M., et al., *J. Appl. Poly Sci.* 2001, 79, 2192-2199; Min, S., et al. *Sen'I Gakkaishi* 1997, 54, 85-92; Nazarov, R. et al., *Biomacromolecules* 2004 May-June; 5(3):718-26. Exemplary organic solvents that can be used to produce the silk solution include, but are not limited to, hexafluoroisopropanol (HFIP). See, for example, International Application No. WO2004/000915, content of which is incorporated herein by reference in its entirety.

The inventors have discovered that molecular weight of silk used for preparing the silk tube can have an effect on properties of the silk tube, such as swelling ratio, degradation, drug release kinetics and the like.

Silk fibroin solution for forming the silk tubes or for coating the clamped portions of the silk tube can have a silk fibroin concentration of from about 1% to about 50% (w/v). In some embodiments, the silk fibroin solution has a silk fibroin concentration of from about 10% to about 40% or from 15% to about 35% (w/v). In one embodiment, the silk fibroin solution has a silk fibroin concentration of from about 20% to about 30% (w/v). In one embodiment, the silk fibroin solution has a silk fibroin concentration of about 30% (w/v). In some embodiments, the silk fibroin solution has a silk fibroin concentration of about 0.1% to about 30% (w/v), about 0.5% to about 15% (w/v), about 1% to about 8% (w/v), or about 1.5% to about 5% (w/v). In some embodiments, the silk fibroin solution has a silk fibroin concentration of about 5% to about 30% (w/v), about 10% to about 25% (w/v), or about 15 to about 20%(w/v). The silk fibroin solution used for coating the clamped portions is also referred to as a "silk coating solution" herein.

The silk fibroin for making the silk tubes can be modified for different applications or desired mechanical or chemical properties of the silk tube. One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein. Additionally, the silk matrix can be combined with a chemical, such as glycerol, that, e.g., affects flexibility and/or solubility of the matrix. See, e.g., WO 2010/042798, Modified Silk films Containing Glycerol.

Optionally, the conformation of the silk fibroin in the tube, prepared using any method, can be further altered after formation. Without wishing to be bound by a theory, the induced conformational change alters the crystallinity of the silk fibroin in the tube, e.g., Silk II beta-sheet crystanllinity. This can alter the rate of release of the therapeutic agent from the silk fibroin tube. The conformational change can be induced by any methods known in the art, including, but not limited to, alcohol immersion (e.g., ethanol, methanol), water annealing, heating annealing, shear stress, ultrasound (e.g., by sonication), pH reduction (e.g., pH titration and/or exposing a silk matrix to an electric field) and any combinations thereof. For example, the conformational change can be induced by one or more methods, including but not limited to, controlled slow drying (Lu et al., 10 Biomacromolecules 1032 (2009)); water annealing (Jin et al., Water-Stable Silk Films with Reduced β-Sheet Content, 15 Adv. Funct. Mats. 1241 (2005); Hu et al. Regulation of Silk Material Structure by Temperature-Controlled Water Vapor Annealing, 12 Biomacromolecules 1686 (2011)); stretching (Demura & Asakura, Immobilization of glucose oxidase with Bombyx mori silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposing a silk matrix to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, the conformation of the silk fibroin in the silk-based delivery system can be altered by water annealing. For example, the silk-based tube can be subjected to water vapor annealing, before, during, or after loading of the therapeutic agent. Without wishing to be bound by a theory, it is believed that physical temperature-controlled water vapor annealing (TCWVA) provides a simple and effective method to obtain refined control of the molecular structure of silk biomaterials, e.g., silk tubes disclosed herein. The silk materials can be prepared with control of crystallinity, from a low content using conditions at 4° C. (a helix dominated silk I structure), to highest content of ~60% crystallinity at 100° C. (β-sheet dominated silk II structure). This physical approach covers the range of structures previously reported to govern crystallization during the fabrication of silk materials, yet offers a simpler, green chemistry, approach with tight control of reproducibility. Temperature controlled water vapor annealing is described, for example, in Hu et al., Rergulation of Silk Material Strcuture By Temperature Controlled Water Vapor Annealing, Biomacromolecules, 2011, 12(5): 1686-1696, content of which is incorporated herein by reference in its entirety.

In some embodiments, the silk tube can be treated with an alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is about 90%.

Alternatively, the alteration in the conformation of the silk fibroin in the tube can be induced by treating the tube with sheer stress. The sheer stress can be applied, for example, by passing the tube through a needle. Other methods of inducing conformational changes include contacting the tube with an electric field, salt or by applying pressure.

Without limitations, the silk tube can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk in the silk tube is present completely in a silk II beta-sheet conformation, i.e., 100% silk II beta-sheet crystallinity.

In some embodiments, the silk fibroin solution for preparing the film-spun silk tube can comprise one or more (e.g., one, two, three, four, five or more) additives.

Without limitations, an additive can be selected from small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. Total amount of additives in the solution can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the solution.

In some embodiments, an additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. No. 6,302,848; U.S. Pat. No. 6,395,734; U.S. Pat. No. 6,127,143; U.S. Pat. No. 5,263,992; U.S. Pat. No. 6,379,690; U.S. Pat. No. 5,015,476; U.S. Pat. No. 4,806,355; U.S. Pat. No. 6,372,244; U.S. Pat. No. 6,310,188; U.S. Pat. No. 5,093,489; U.S. Pat. No. 387,413; U.S. Pat. No. 6,325,810; U.S. Pat. No. 6,337,198; U.S. Pat. No. 6,267,776; U.S. Pat. No. 5,576,881; U.S. Pat. No. 6,245,537; U.S. Pat. No. 5,902,800; and U.S. Pat. No. 5,270,419, content of all of which is incorporated herein by reference.

Other additives suitable for use with the present disclosure include biologically or pharmaceutically active compounds. Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-β1, and the like.

In some embodiments, the silk fibroin solution for making the film-spun silk tube or coating the ends comprises one or more therapeutic agents. The therapeutic agent in the solution can be same or different from that is to be encapsulated in the silk tube.

In some embodiments, the silk tube can be porous, e.g., the wall of the silk tube can be porous. For example, the silk tube can have a porosity of at least about 30%, at least about 40%, at least about 50%, at least about 60%, at least about 70%, at least about 80%, at least about 90%, or higher. Too high porosity can yield a silk tube with lower mechanical properties, but with faster release of a therapeutic agent. However, too low porosity can decrease the release of a therapeutic agent. One of skill in the art can adjust the porosity accordingly, based on a number of factors such as, but not limited to, desired release rates, molecular size and/or diffusion coefficient of the therapeutic agent, and/or concentrations and/or amounts of silk fibroin in the silk tube. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous silk tube can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the pores of a silk tube can have a size distribution ranging from about 50 nm to about 1000 µm, from about 250 nm to about 500 µm, from about 500 nm to about 250 µm, from about 1 µm to about 200 µm, from about 10 µm to about 150 µm, or from about 50 µm to about 100 µm. In some embodiments, the silk fibroin can be swellable when the silk fibroin tube is hydrated. The sizes of the pores can then change depending on the water content in the silk fibroin. The pores can be filled with a fluid such as water or air.

Methods for forming pores in a silk matrix are known in the art, e.g., porogen-leaching method, freeze-drying method, and/or gas-forming method. Such methods are described, e.g., in U.S. Pat. App. Nos.: US 2010/0279112, US 2010/0279112, and U.S. Pat. No. 7,842,780, the contents of which are incorporated herein by reference in their entirety.

Though not meant to be bound by a theory, silk tube porosity, structure and mechanical properties can be controlled via different post-spinning processes such as vapour annealingheat treatment, alcohol treatment, air-drying, lyophilization and the like. Additionally, any desirable release rates, profiles or kinetics of the therapeutic agent can be controlled by varying processing parameters, such as film thickness, silk molecular weight, concentration of silk in the silk tube, beta-sheet conformation structures, silk II beta-sheet crystallinity, or porosity and pore sizes.

Method for the Preparation of Silk Reservoir Implants or Injectable Silk Reservoirs For loading into the silk tubes, a therapeutic agent can be in any form suitable for the particular method to be used for loading. For example, the therapeutic agent can be in the form of a solid, liquid, or gel. In some embodiments, the therapeutic agent is in the form of a solution, powder, a compressed powder or a pellet. In some embodiments, the therapeutic agent can be encapsulated in a silk fibroin particle for loading into the silk tubes. The therapeutic agent can be encapsulated in a silk matrix, e.g., by blending the therapeutic agent into a silk solution before processing into a desired material state, e.g., a microsphere or a nanosphere for loading into the silk tube. Silk fibroin particles (e.g., microspheres or nanospheres) which encapsulate a therapeutic agent are described, for example, in U.S. Pat. No. 8,187,616; and U.S. Pat. App. Pub. Nos. US 2008/0085272, US 2010/0028451, US 2012/0052124, US 2012/0070427, US 2012/0187591, the content of all of which is incorporated herein by reference.

In some embodiments, the therapeutic agent is encapsulated in a silk tube based composition described herein, i.e., the silk reservoir implant or silk injectable reservoir comprises a silk tube in which are loaded other silk tubes comprising the therapeutic agent.

In some embodiments, the silk tube can be optionally hydrated before loading with the therapeutic agent. For example, the silk tube can be incubated in deionized water until completely hydrated. In some embodiments, the silk tube can be incubated in deionized water for 5, 10, 15, 20, 30, 45, 60, 90, 120, 150, 180, 210, 240, 270, 300 minutes or more. The tube can be hydrated at room temperature or at higher temperatures. Accordingly, in some embodiments, the tube can be hydrated at a temperature from about 15° C. to about 80° C. In some embodiments, the tube can be hydrated at a temperature about 60° C. Without wishing to be bound by a theory, hydrating the silk tube before loading can swell or soften the tube thus promoting loading.

In some embodiments, the silk tube can be open at both ends during loading. In this case, the hydrated silk tube can be held horizontally using tweezers, while the therapeutic agent is loaded from one end in solution, powder or pellet format using an appropriately sized pipetter, spatula or tweezers, respectively. In some embodiments, one end of the tube can be clamped before loading of the therapeutic agent using for example, pinch valves, clips or wrenches. The tube clamped on one end can be held vertically, while the therapeutic agent is loaded from the open end in solution, powder or pellet format using an appropriately sized pipetter, spatula or tweezers, respectively. Following loading, the open end(s) of the tube can be clamped using for example, pinch valves, clips or wrenches.

Following loading of therapeutic agent, clamped, hydrated silk tubes can be dried at a suitable temperature (e.g., 20° C. or higher temperatures) in ambient conditions for a suitable duration (e.g. 30 min or longer) to allow complete drying of the tube and the loaded therapeutic agent. Alternatively, clamped, hydrated silk tubes can be dried under accelerated drying conditions (e.g. in vacuum, or under gas flow for a suitable duration to allow complete drying of the tube and the loaded drug (e.g. for 10 min or longer). Drying conditions can be selected to maximize stability of the therapeutic agent.

After drying, the closed ends of the silk tube can be coated with a silk fibroin solution, e.g., via dip coating to obtain silk reservoir implants or silk injectable reservoirs. Dip coating can be repeated several times until the desired coating thickness is achieved. Without wishing to be bound by a theory, coating the closed ends helps in forming a tight seal and prevents dose dumping. The tube ends can be coated with a silk fibroin solution using any method known in the art. For example, the silk fibroin solution can be sprayed on the closed ends or the closed ends dipped into the silk fibroin solution. In one embodiment, closed ends of the tube are dipped into a silk fibroin.

All aforementioned steps to produce silk reservoir implants or silk injectable reservoirs can be performed under aseptic conditions. For example, the film spinning, methanol treatment or water annealing, hydration, drug loading, heat treatment and dip coating procedures can be conducted aseptically inside a laminar flow hood.

In one embodiment, loading of the pharmaceutically active agent into silk tubes to prepare silk reservoir implants or silk injectable reservoirs comprises: (i) hydrating the silk tube; (ii) loading the therapeutic agent into the tube and tube end clamping; (iii) drying the silk tube; and (iv) dip coating of tube ends.

The silk-based drug delivery described herein can be sterilized using conventional sterilization process such as radiation based sterilization (i.e. gamma-ray), chemical based sterilization (ethylene oxide), autoclaving, or other appropriate procedures. In some embodiments, sterilization process can be with ethylene oxide at a temperature between from about 52° C. to about 55° C. for a time of 8 or less hours. The silk based drug delivery can also be processed aseptically. Sterile drug delivery composition can packaged in an appropriate sterilize moisture resistant package for shipment.

An Embodiment of Method for Preparing the Silk Based Drug-Delivery System

In one embodiment, a silk solution having a silk concentration of 8 wt % or more (desirably about 30 wt %) is injected through a narrow gauge needle ($\geq 21$ G) onto a wire which is concomitantly reciprocated horizontally while being rotated along its axis to form a silk coating thereon, wherein a syringe pump controls the flow rate of the injected silk solution. The silk coating is then heated, while rotating the wire, to form a silk film. Notably, rotation of the wire during heat treatment promotes uniformity of the silk film thickness. The injecting/heating steps are optionally repeated until the desired diameter is achieved. The overall dimensions of the silk compositions, from injectable to implantable size range, morphology, and structure of the silk compositions can be varied as desired. In one embodiment, silk II beta-sheet crystallinity is induced in the silk composition (e.g., by soaking in 90:10 (vol/vol) methanol:water) followed by hydration thereof (e.g., by incubating in deionized water until complete film hydration). The resultant silk compositions are removed from the wire and cut to the desired length.

The silk tubes are loaded with therapeutic agent in powder, pellet or liquid form or the therapeutic agent is encapsulated in a particle (e.g., a microsphere or a nanosphere) while one end of the silk tube is clamped. Following loading of therapeutic agent, the film-spun silk tube is clamped at the other end and allowed to dry at a suitable temperature (e.g., 20° C. or higher temperatures) in ambient conditions for a suitable duration to allow complete drying of the tube and the loaded drug (e.g. overnight or longer), or under accelerated drying conditions (e.g. in vacuum, or under gas flow for a suitable duration to allow complete drying of the tube and the loaded therapeutic agent (e.g. for 10 min or for longer durations). Drying conditions are selected to maximize stability of the therapeutic agent. Silk reservoir implants or injectable silk reservoirs are formed by clamping both ends of the silk tube and their subsequent coating (e.g., by dip-coating the ends) using a silk solution having a silk concentration of 8 wt % or higher to ensure a tight seal and prevent dose dumping.

In some embodiments, two or more different therapeutic agents can be loaded in the silk tube. When two or more different therapeutic agents are loaded, they can be loaded simultaneously, one after the other, or any combinations thereof. In addition, the different therapeutic agents can be loaded in same amount, in different amounts, or any combinations thereof.

Therapeutic Agents

Generally, any therapeutic agent can be encapsulated in the silk tube. As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof, including, for example, DNAnanoplexes.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocriptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

In some embodiments, the therapeutic agent can be selected from the group consisting of 1018 immunostimulatory sequence (1018-iss), humanized A33 antibody (1311-hua33), 13-cis-retinoic acid, fludeoxyglucose 18F (18f-fdg), human monoclonal antibody 1d09c3, 2-pentenylpenicillin, DNA vaccines, e.g., 825780 dna antiviral vaccine (by GlaxoSmithKline), topical antibiotics used for bacterial infections, e.g., A/T/S®, by BKK Pharmaceuticals LLC, Wilmington, Del., erythromycin, a-1 antitrypsin, abacivir; lamivudine, abarelix, abatacept, abciximab, abetimus sodium, Anti-MCP-1 monoclonal antibody (e.g., abn 912, by Novartis), anti L-12/23 antibodies, e.g., abt 325/abt 874 by Abbott Laboratories, abx-i18, autologous cell vaccines, e.g., AC VACCINE TECHNOLOGY®, by AVAX Technologies, peptide YY3-36 (e.g., ac162352, by Curis), glucagon-like peptide-1-amylin (GLP-1-amylin e.g., ac2592, by Amylin Pharmaceuticals), acadesine, acamprosate, acarbore, acarbose, acatophenazine, immunotherapeutic vaccines, e.g., vanutide cridificar, acebutolol, acebutolol hydrochloride, aceclofenac, acetamide, acetaminophen, aspirin;caffeine, acetaminophen;butalbitol, acetaminophen;codeine phosphate, acetazolamide, acetazolamide sodium, acetic acid, acetic acid hydrocortisone, acetohexamide, acetohydroxamic acid, acetophenazine, acetyl sulfisoxazole, acetylcholine chloride, acetylcysteine, acetylsalicylic acid, acid glycoprotein, acitretin, aclometasone, acrivastine;pseudoephedrine, tocilizumab, for example, ACTEMRA® (sold by Genentech), adrenocorticotropic hormone (acth), activated recombinant factor vii, acyclovir, acyclovir sodium, adalimumab, adapalene, adefovir dipivoxil, ademetionine, adenine, adeno associated viral vector, adenosine, adenoviral vector, adenovirus, adenovirus p53 (e.g., ADVEXIN®, by Introgen Therapeutics. Inc.), adinazolam, adiponectin, adpedf, adrafinil, adrenaline, adrenocorticotropic hormone, advate antihemophilic factor plasma/albumin-free method, XIAP antisense oligonucleotides (e.g. aeg 35156, by Aegera Therapeutics), afelimomab, anti-herpes vaccines, e.g., ag-707, by Antigenics, agalsidase alpha, agalsidase beta, aglucosidase alpha, ags-psca mab (monoclonal antibody to prostate stem cell antigen), alpha-1 antitrypsin deficiency gene therapy (e.g., agtc 0106, by Applied Genetic Technologies Corp.), ahnotriptan, albendazole, albumin iodinated i-125 serum, albumin iodinated i-131 serum, albumin, human, albuterol, albuterol sulfate, albuterol;ipatropium, alclometasone dipropionate, alcohol, aldesleukin, aldesleukin, interleukin-2 (IL2), aldosterone, alefacept, alemtuzumab, alendronate, alendronic acid;colecalciferol, alfentanil, alfentanil hcl, alfentanil hydrochloride, Alferon N Injection, for example, ALFERON N INJECTION® (sold by Hemispherx Biopharma, Inc.), alfimeprase, alfuzosin, alfuzosin hcl, alglucerase, alicaforsen, alitretinoin, alizapride, allopurinol, allopurinol sodium, gene therapy for cancer, e.g., ALLOVECTIN-7® (developed by Vical Inc.), allylprodine, alminoprofen, almotriptan, alosetron hcl, alperopride, alpha-1 antitrypsin, alpha-1 proteinase inhibitor, alpha-galactosidase a, alphaprodine, alpidem, alprazolam, alprostadil, alseroxion, alteplase (tpa), altretamine, long acting human growth hormone (e.g., altu-238, by Altus Pharmaceuticals), aluminum hydroxide, aluminum hydroxide;magnesium carbonate, melanoma, HIV, and cancer vaccines, e.g., alvac gp 100, alvac mn120 tmgmp, and alvaccea/b7.1 (developed by Sanofi Pasteur), amantadine, amantadine hydrochloride, ambenonium chloride, ambrisentan, amcinonide, humanized monoclonal antibodies that recognize human TNF-alpha, e.g., ame 527, developed by Applied Molecular Evolution, Inc.), amerscaen medronate ii, amerscam stannous agent, amerscan hepatate ii, amesergide, amfenac, fully human antibodies, e.g., amg 108/amg 531/amg 623/amg 714, amg 221 (inhibitor of 11 beta-hydroxysteroid dehydrogenase type 1), amg 317 (IL-4Ralpha antagonist), amg 403 (human anti-nerve growth factor monoclonal antibody), amg 517 (TRPV1 antagonist), amg102/amg 386/amg 479/amg 623/amg 655/amg 706, developed by Amgen, amifostine, amikacin sodium, amikacin sulfate, amiloride hydrochloride, amiloride hydrochloride dihydrate, amino acids, amino acids; glycerin; electrolytes, amino alcohol, aminoacetic acid, aminocaproic acid, aminoglutethimide, aminohippurate sodium, aminolevulinic acid, aminolevulinic acid hydrochloride, aminophylline, aminopropylon, aminosalicylic acid, amiodarone, amiodarone hcl, amiodarone hydrochloride, amisulpride, amitriptyline, amitriptyline hydrochloride, amitriptyline;chlordiazipoxide, amixetrine, amlexanox, amlodipine, amlodipine besylate, amlodipine;atorvastatin, amlodipine; benazepril, ammonium chloride, ammonium lactate, amobarbital sodium;ecobarbital sodium, amoxapine, amoxicillin, amoxicillin;clarithromycin; lansoprazole, amperozide, amphenidone, amphetamine, amphetamine; dextroamphetamine, amphotericin b, ampicillin, ampicillin and sulbactam, ampicillin sodium, ampicillin trihydrate, ampicillin;clavulonate, amprenavir, amrinone lactate, amylin, amylpenicillin, amytal sodium, anagrelide hydrochloride, anakinra, anastrazole, andropinirole, androstenedione, human collagen derivatives, for example, ANGIOCOL® (by BioStratum, Inc.), angiotensinogen, anidulafungin, anileridine, anisindione, radionucleotides for imaging, for example, AN-SULFUR COLLOID® (by Mallinckrodt Pharmaceuticals), monoclonal antibodies specific for human CD16, monoclonal antibodies specific for human CD 23 monoclonal antibody specific for human CD3 on T cells, monoclonal antibodies specific for CD80, antidiuretic hormone, antihemophelic factor (factor viii), antihemophilic factor (recombinant), monoclonal antibodies specific for HIV-1, monoclonal antibodies specific for hsp90, anti-idiotype cancer vaccine, anti-ige antibodies, anti-il-4 antibodies, anti-inhibitor coagulant complex, anti-interferon-gamma, anti-lfa-1 antibodies, mouse, anti-human, monoclonal antibody, anti-lymphotoxin beta receptor mab, antimullerian hormone, anti-pem mab, antisense oligonucleotide, anti-staph mab, anti-tac(fv)-pe38 immunotoxin, antivenin crotalidae polyvalent injection, antivenin lactrodectus mactans, antivenin micrurus fulvius, apazone, apc8024, aplidine, apo21/trial (amg 951), apo-cilazapril/hctz, apo-digoxin, apo-etidronate, apo-feno-super, apo-flecainide, apomorphine hydrochloride injection, for example, APOKYN® (sold by Mylan), apo-levetiracetam, apo-medroxy, apo-meloxicam, apo-methotrexate, apo-metoprolol sr, apo-midodrine, apo-mirtazapine, apomorphine, apomorphine hydrochloride, apomorphinediacetate, apo-omeprazole, apo-ondansetron, apo-oxcarbazepine, apo-ramipril, apo-ranitidine, apo-risperidone, apo-sumatriptan, apo-topiramate, apraclonidine, aprepitant, aprotinin bovine, argatroban, arginine hydrochloride, arimoclomol, aripiprazole, arsenic trioxide, articaine hydrochloride/epinephrine, asparaginase, aspirin, aspirin; caffeine; orphenadrine citrate, dipyridamole, hydrocodeine; hydrocodone, meprobamate, aspirin; pravastatin, high affinity α3β4 nAChR ligands, for example, at-1001 (by Alba Therapeutics), atazanivir sulfate, atenolol, atenolol; chlorthalidone, 2'-MOE-modified antisense oligonucleotide (ASO) targeting human IGF-IR, for example, atl 1101 by Antisense Therapeutics, antisense inhibitors of CD 49d, for example, atl 1102 by Antisense Therapeutics, atomoxetine, atorvastatin calcium, atovaquone, atovaquone; proguanil hcl, atracurium besylate, atrial natriuretic peptide, atropine sulfate, atropine sulfate/edrophonium chloride, attenuated live measles vaccine, attenuated rotavirus vaccine, auranofin, aurexis tefibazumab, autologous renal cell tumor vaccine, autologous tumor, autologus gp100-reactive pbl and til plus rf-gp100p209, ave 0005, ave 9633 maytansin-loaded anti-cd 33 mab, avi-4065, aviptadil, avr 118, avx101, azacitidine, azacyclonol, azatadine, azathioprine, azathioprine sodium, azelaic acid, azelastine, azelastine hcl, azidocillin, azithromycin, azidothymidine, for example, AZT® by Burroughs Wellcome Company; lamivudine, for example 3TC® by GlaxoSmithKline;abacavir, aztreonam, aztreonam lysinate, bacampicillin, bacille calmette-guerin, bacitracin, bacitracin zinc, bacitracin; polymyxin b sulfate, baclofen, bacterial lipase, bacteriostatic sodium chloride, bacteriostatic water, BAPINEUZUMAB®(sold by Pfizer), barium sulfate, basiliximab, bavituximab, bcl-2 antisense oligonucleotide, bcl-2 antisense oligonucleotides, for example, g-3139 (by Genta Incorporated), becaplermin, becatecarin, beclomethasone dipropionate, belatacept, benactyzine, benazepril hydrochloride, benazepril; hydrochlorothiazide, bendroflumethiazide, bendroflumethiazide; nadolol, benmoxine, benoxaprofen, benperidol, benserazide, bentoquatam, BENZAMYCIN® (sold by Dermik Laboratories), benzoic acid, benzonatate, benzoyl peroxide, benzoyl peroxide;clindamycin, benzphetamine, benzphetamine; diethylproprion, benzpiperylon, benzquinamide, benzquinamide hydrochloride, benztropine, benztropine mesylate, benzydramine, benzylmorphine, benzylpenicillin, beractant, bertezomib, beta-2 adrenergic agonist, for example, BETA-2® (sold by Nephron Pharmaceuticals Corporation), betahistine, betaine, betaine anhydrous, betamethasone acetate, betamethasone dipropionate, betamethasone sodium phosphate, betamethasone valerate, interferon beta-1b, for example, BETASERON® (sold by Bayer Healthcare Pharmaceuticals. Inc.), betaxolol, betaxolol hydrochloride, bethanechol chloride, bevacizumab, bexarotene, bezitramide, bicalutamide, bimatoprost, bimosiamose disodium, binedaline, biperiden, biphasic insulin aspart, bisoprolol fumarate, bitolterol, bitolterol mesylate, bivalirudin, bivatuzumab, bleomycin, bleomycin sulfate, aloha interferon derivatives, for example, blx 883 by Biolex Therapeutics, bortezomib, bosentan, botulinum toxin type a+b, bovine bile extract, BAFF antagonists, for example, br3-fc by Biogen Idea/Genentech, bretylium tosylate, brimonidine tartrate, brinzolamide, brofaromine, bromelain; vitamin c; L-glutamine; quercetin, bromfenac, bromisovalum, bromocriptine, bromocriptine mesylate, bromodiphenhydramine; codeine, bromopheniramine; dextromethorphin; pseudoephedrine, bromopheniramine; pseudophedrine, bromopheniramine; pseuodophedrine, bromopride, bromperidol, brompheniramine, brompheniramine maleate, brucine, buclizine, budesonide, budesonide; formoterol fumarate, budesonide; formoterol, budipine, bufexamac, buffered intrathecal electrolytes/dextrose, bumetanide, bupivacaine hydrochloride, bupivacaine hydrochloride/epinephrine, bupivacaine hydrochloride/epinephrine bitartrate, bupivocaine;lidocaine, buprenorphine, buprenorphine hydrochloride, buprenorphine hydrochloride/naloxone hydrochloride, bupropion, bupropion hydrochloride, buramate, busalazide disodium, buserelin, buspirone, buspirone hydrochloride, busulfan, butabarbital, butaclamol, butalbital, butalbital; acetaminophen, butalbital; acetaminophen; caffeine, butalbital; apap, butalbital; butanamide, butaperazine, butenafine hcl, butoconazole nitrate, butorphanol, butorphanol tartrate, butriptyline, fosbretabulin, for example, ca4p by Mateon Therapeutics, cabergoline, caffeine, caffeine citrate, caffeine; ergotamine, cold adapted influenza vaccines, for example, caiv-t by Aviron, calciferol, calcipotriene, calcitonin, calcitonin salmon, calcitriol, calcium acetate, calcium carbonate; residronate, calcium chloride, calcium disodium versenate, calcium gluconate, calcium-n-carboamoylaspartate, calfactant, candesartan, cannobinoids, capecitabine, capreomycin sulfate, capromab pendetide, captodiamine, captopril, captopril; hctz, capuride, carbachol, carbamazepine, carbamic acid, carbcloral, carbenicillin, carbidopa, carbidopa; levodopa, carbinoxamine maleate, carbiphene, mepivacaine, for example, CARBOCAINE® (sold by Hospira Worldwide, Inc), carbon 13 urea, carbon 14 urea, carboplatin, carboprost tromethamine, carboxylic acid, carboxypeptidase, carbromal, cardioplegic solution, cardiotrophin-1, carfecillin, carindacillin, carisoprodol, carmustine, caroxazone, carphenazine, carpipramine, carprofen, carteolol hydrochloride, carvedilol, caspofungin acetate, caspofungin msd, anti-CD22 immunotoxins, for example, cat 3888, by Genecor, catumaxomab, cord blood-derived stem cell therapies, for example, cb 001 by ViaCell, clara cell 10 kD protein (cc10), monoclonal antibodies specific to c-c chemokine receptor type 5 (ccr5 mab), anti-VEGFR-2 antibodies, for example, cdp 791 by ImClone Systems, cefaclor, cefadroxil, cefamandole, cefazolin, cefazolin sodium, cefdinir, cefditoren pivoxil, cefepime hydrochloride, cefibutin, cefinetazole, cefixime, cefinetazole, cefoperazone, cefotaxime, cefotaxime sodium, cefotetan, cefoxitin, cefoxitin sodium, cefpodoxime proxetil, cefprozil, ceftazidime, ceftazidime sodium, ceftriaxone, ceftriaxone sodium, cefuroxime, cefuroxime axetil, cefuroxime sodium, celecoxib, cell therapy, cellular implant therapy, cephacetrile, cephalexin, cephaloglycin, cephaloridine, cephalosporin c, cephalosporins, cephalotin, cephamycin a, cephamycin b, cephamycin c, cephamycins, cepharin, cephradine, adenoviral vectors for the treatment of Alzheimer's Disease, for example, cere-110 by Sangamo Biosciences, Inc., adenoviral vectors for the treatment of Parkinson's Disease, for example, cere-120 by Sangamo Biosciences, Inc., CEREDASE® (sold by Genzyme Corporation), CERETEC® (sold by GE Healthcare), cericlamine, certolizumab pegol, ceti-1 vaccine, cetrizine, cetrorelix, cetuximab, cevimeline hcl, cevimeline hcl, chimeric mab, chimeric monoclonal antibody, chimeric tumor-necrosis therapy (tnt), chimeric-anti-interleukin-6 monoclonal antibody, lucatumumab, for example, chir-12.12 by Xoma Corp., chloralbetaine, chlorambucil, chloramphenicol, chloramphenicol sodium succinate, chlordiazepoxide, chlorhexidine gluconate, chlorobutinpenicillin, chloramphenicol, for example, CHLOROMYCETIN® (sold by Pfizer, Inc.), chloroprocaine, chloroprocaine hydrochloride, chloroquine phosphate, chlorothiazide, chlorothiazide sodium, chloroxine, chlorpheniramine, chlorpheniramine; hydrocodone, chlorpromazine, chlorpromazine hydrochloride, chlorpromazine hydrochloride intensol, chlorpropamide, chlorprothixene, chlorthalidone, chlorthiazide; reserpine, chlorzoxazone, cholecystokinin, cholest-4-en-3-one, oxime, cholestyramine, cholic acid, choline, choriogonadotropin alfa, chorionic gonadotropin, chromic chloride, chromic phosphate p32, chromitope sodium, ciclesonide, ciclopirox, ciclopirox olamine, cicloprilax, ciclosporin, cidofovir, cilazaprol, cilengitide, cilostazol, cimetidine, cimetidine hydrochloride, cinacalcet, cinchophen, cinmetacin, cinnarizine, cipramadol, ciprofloxacin, ciprofloxacin hydrochloride, dexamtheasone, cisatracurium besylate, injectable forms of medronic acid, for example, CIS-MDP® (sold by CIS-US. Inc.), cisplatin, cisplatin/5-fu therapy, citalopram, citalopram hydrobromide, cladribine, clarithromycin, clebopride, clemastine, clemastine fumarate, clindamycin hydrochloride, clindamycin injection, usp, clindamycin phosphate, clindamycin; benzoyl peroxide, clioquinol, clioquinol; hydrocortisone, clobenzepam, clobetasol, clobetasol propionate, clocapramine, clocortolone pivalate, clofarabine, clofibrate, clomacran, clometacin, clometocillin, clomiphene citrate, clomipramine, clomipramine hydrochloride, clonazepam, clonidine, clonidine hydrochloride, clonidine;chlorthalidone, clonitazene, clonixin, clopenthixol, clopidogrel, clopriac, clorazepate dipotassium, clospirazine, clothiapine, clotrimazole, clotrimazole;betamethasone, clovoxamine, cloxacillin, cloxacillin sodium, clozapine, inotuzumab ozogamicin, for example, cmc-544 by Pfizer, humanized immunotoxins against Lewis Y antigen, for example, cmd-193 by Wyeth, ustekinumab, for example, cnto 1275 by Cenotor, Inc, siltuximab, for example, cnto 328 by Janssen Biotech, Inc., co bicalutamide, co cilazapril, co fluconazole, co fosinopril, co ipra-sal, co risperidone, co salbut-iprat inhalation solution, co topiramate, cobalt chloride, codeine, codeine phosphate, codeine; chlorpheniramine, colchicines; probenicid, colesevelam hcl, colestipol hcl, colfosceril palmitate, colistimethate, colistimethate sodium, collagenase, prochloroperazine, for example, COMPAZINE® (sold by GlaxoSmithKline), conivaptan hydrochloride, copper, corticorelin ovine triflutate, corticotropin, corticotropin-releasing hormone, cortisone acetate, co-sertraline, cotinine, cp-547, 632, cp-751, 871, cpg 7909, cr0002, crisantaspase, cromolyn sodium, cromolyn sulfate, crotamiton, cs 1008, ctg cca cgt tct cct gc-, cupric chloride, cyamemazine, cyanocobalamin, cyclacillin, cyclizine, cyclobenzaprine, cyclobenzaprine hydrochloride, cyclopentolate hydrochloride, cyclopentolate;phenylephrine, cyclophosphamide, cyclosporin, cyclosporin a, cyclosporine, cyproheptadine, cyproheptadine hydrochloride, cysteinyl leukotrienes, cytarabine, cytomegalovirus immune globulin (cmv-igiv), dacarbazine, daclizumab, dactinomycin, dalteparin sodium, danazol, dantrolene sodium, dapsone, daptomycin, darbepoetin alpha, darifenacin hcl, darunavir, dasatinib, daunorubicin citrate, daunorubicin hydrochloride (plus liposomal), desmopressin, for example, DDAVP® (sold by Ferring Pharmaceuticals), decitabine, deferiprone, deferoxamine mesylate, defibrotide, dehydroepiandrosterone, delavirdine mesylate, demeclocycline hydrochloride, dendritic cell vaccine, denileukin diftitox, denosumab, denufosol tetrasodium, deoxygalactonojirimycin hydrochloride, deoxyribose phosphorothioate, deprenyl, desflurane, desipramine, desipramine hydrochloride, desirudin, desirudin recombinant, desloratadine, desmodus rotundus salivary plasminogen activator (dspa), desmopressin acetate, desogestrel, desogestrel; ethinyl estradiol, desonide, desoximetasone, deuterium oxide, dexamethasone, dexamethasone intensol, dexamethasone sodium phosphate, dexchlorpheniramine maleate, dexfenfluramine, dexmedetomidine, dexmethylphenidate hcl, dexrazoxane, dexrazoxane hydrochloride, dextramethorphan; guafenisin; pseudophedrine, dextroamphetamine, dextroamphetamine saccharate, dextroamphetamine sulfate, dextromethorphan, dextromoramide, dextropropoxyphene, dextrose, dextrose dialysis solution, diaminopyridine phosphate, diamorphine, diatrizoate meglumine, diatrizoate sodium, diazepam, diazoxide, phenoxybenzamine, for example, DIBENZYLINE® (sold by Concordia Pharmaceuticals, Inc.), dibotermin alpha, diclofenac, diclofenac;misoprostol, dicloxacillin, dicloxacillin sodium, dicyclomine hydrochloride, didanosine, diethylpropion, difenoxin; atropine, diflorasone diacetate, diflunisal, digoxin, dihydrocodeine, dihydroergokryptine, dihydroergotamine, dihydroergotamine mesylate, diltiazem, diltiazem hydrochloride, dimenhydrinate, dimercaprol, dimethyl sulfoxide, dimethylphenidate, dinaprostone, dinoprostone, diphenhydramine, diphenhydramine hydrochloride, diphenicillin, diphenidol, diphenoxylate, diphenoxylate;atropine, diphenylcyclopropenone, diphtheria/tetanus/pertussis/hepatitis b vaccine, diphtheria/tetanus/pertussis/hepatitis b/poliomylelitis vaccine, diphylline, dipipanone, dipivefrin hydrochloride, diptheria/tetanus/hepatitis b/poliomyelitis/hib/perutssis vaccine, dipyridamole, disopyramide phosphate, disulfiram, dmsa, dna nanoparticle gene therapy, dna vaccine, dnase, dobutamine hydrochloride, docetaxel, docosahexaenoic acid, docosanol, dofetilide, dolasetron mesylate monohydrate, dolasetronmethanesulfonate, dolophine hydrochloride, dom-alendronate, domalendronate, dom-anagrelide, dom-bicalutamide, dom-citalopram, dom-doxycycline, domeridone, dom-hydrochlorothiazide, dom-mirtazapine, dom-ondanssetron, domrisperidone, dom-simvastatin, dom-ursodiol c, donepezil, dopamine, dopamine hydrochloride, dornase alfa, dorzolamide, dorzolamide; timolol, dosulepin, doxacalciferol, doxapram hydrochloride, doxazosin mesylate, doxepin, doxepin hydrochloride, doxorubicin, doxorubicin carbon/iron, doxorubicin hydrochloride, doxorubicin polyisohexylcyanoacrylate nanoparticles, doxycycline, doxycycline hyclate, doxylamine, doxylamine succinate, dronabinol, droperidol, droprenilamin hcl, drospirenone; estradiol, drosporenone; ethinyl estradiol, drotrecogin alpha, dtp vaccine, diethylenetriaminepentaacetid acid (dtpa), duloxetine, tetracycline hydrochloride, for example, DURAMYCIN® (sold by Durvet Animal Products, Inc.), dutasteride, dx-88 (plasma kallikrein inhibitor), dx-890 (human neutrophil elastase inhibitor), dyphylline, e. coli heat-shock protein 70 with bovine retinal s-antigen, e.e.s. erythromycin, ethylsuccinate, econazole nitrate, ecromeximab, ecteinascidin 743, eculizumab, edetate calcium disodium, edetate disodium, edrophonium chloride, efalizumab, efavirenz, eflornithine, egen-001 (IL-2 plasmid formulated with PEG-PEI-cholesterol lipopolymer), electrolyte irrigation solution, eletriptan, eliprodil, emd 273063 antibody/cytokine fusion protein comprised of a humanized version of the murine anti-GD2 antibody 14.18 coupled to two molecules of IL-2), emedastine difumarate, emtricitabine, enalapril, enalapril maleate, enalapril maleate; felodipine, enalapril; diltiazem, enalaprilat, encirazine, endrophonium chloride, enflurane, enfuvirtide, engineered protein inhibitor of human neutrophil elastase, enoxaparin sodium, entacapone, entecavir, enzastaurin hydrochloride, ephedrine, epinastine hcl, epinephrine, epinephrine, epirubicin hydrochloride, eplerenone, epoetin alfa, erythropoietin (epo-fc), epoprostenol sodium, epothilone b, eprosartan, epstein-barr virus vaccine, eptacog alfa, eptastigmine, eptifibatide, eptotermin alpha, ergocalciferol, ergolinepramipexole, ergoloid mesylates, ergotamine, ergotamine tartrate, ergotamine; caffeine, erlotinib, ertapenem sodium, erythrocin stearate, erythromycin, erythromycin base, erythromycin estolate, erythromycin ethylsuccinate, erythromycin lactobionate, erythromycin stearate, erythromycin;sulfisoxazole, erythropoietin, erythropoietin b, escitalopram, escitalopram oxalate, esmolol hydrochloride, esomeprazole sodium, estazolam, estradiol, estradiol acetate, estradiol cypionate, estradiol hemihydrate and progesterone, estradiol valerate, estradiol;norethindrone, estramustine phosphate, estriol, estrogen;progesterone, estrogens, conjugated, estrogens; medroxyprogesterone, estrone, estropipate, eszopiclone, etamiphyllin, etanercept, etaqualone, ethacrynate sodium, ethacrynic acid, ethambutol, ethambutol hydrochloride, ethanol, ethanolamine oleate, ethiinyl estradiol;ethynadiol acetate, ethinyl estradil; levonorgestrel, ethinyl estradiol, ethinyl estradiol; norethindrone, ethinyl estradiol; levonorgestrel, ethinylestradiol; levonogestrel, ethiodized oil, ethionamide, ethoheptazine, ethosuximide, ethotoin, ethyl eicosopentaenoate, ethynylcytidine, eti-201, etidronate disodium, etilefrin, etodolac, etoposide, etoposide phosphate, eu/3/04/247, exemestane, exenatide lar, exenatide synthetic, extended phenytoin sodium, ezetimibe, factor ix complexes, for example konyne 80, PROFILNINE HEAT-TREATED® by Alpha Therapeutic Corp., proplex sx-t, proplex-t, factor vii, factor viii, factor xi, famciclovir, famotidine, felbamate, felodipine, fenfluramine, fenofibrate, fenoldopam mesylate, fenoprofen calcium, fentanyl, fentanyl citrate, ferumoxides, ferumoxsil, fexofenadine, fexofenadine hydrochloride, fgf-1, fgf-5 peptides, fibrin sealant, fibroblast growth factor 1, fientanyl, filgrastim, finasteride, flavoxate hydrochloride, flecainide acetate, flesinoxan, floxuridine, fluconazole, flucytosine, fludarabine phosphate, fludeoxyglucose, fludeoxyglucose f-18, fludrocortisone acetate, flumazenil, flunisolide, fluocinolone acetonide, fluocinolone; tetrinoin; hydroquinone, fluocinonide, fluoromethalone acetate, fluorometholone, fluorouracil, fluoxetine, fluoxetine hydrochloride, fluoxymesterone, flupenthixol, fluphenazine, fluphenazine decanoate, fluphenazine hydrochloride, flupirtine, flurandrenolide, flurazepam, flurazepam hydrochloride, flurbiprofen, flurbiprofen sodium, fluspirilene, flutamide, fluticasone propionate, fluvastatin, fluvoxamine, fluvoxamine maleate, folic acid, follicle-stimulating hormone, follitropin alfa/beta, fomepizole, fondaparinux sodium, formivirsen, formoterol fumarate, fosamprenavir, fosamprenavir calcium, foscarnet sodium, for example, FOSCAVIR® (sold by Hospira, Inc), fosfomycin; tromethamine, fosinopril, fosinopril sodium, fosphenytoin sodium, frovatriptan, fulvestrant, fumagillin, furosemide, g17(9) gastrin-diphtheria toxoid conjugate, gabapentin, gadobenate dimeglumine, gadodiamide, gadopentetate dimeglumine, gadoteridol, gadoversetamide, GENE-ACTIVATED HUMAN GLUCOCEREBROSIDASE®(ga-gcb, by Shire PLC), galanthamine, gallium citrate ga 67, gallium nitrate, galsulfase, GAMUNEX® (sold by Grifols), ganciclovir, ganciclovir sodium, ganirelix acetate, gentamycin sulfate, for example, GARAMYCIN® (sold by Fera Pharmaceuticals, LLC), gastrin, gatifloxacin, gefitinib, gemcitabine hydrochloride, gemfibrozil, gemifloxacin mesylate, gemtuzumab ozofamicin, gene therapy, gentamicin, gentamicin sulfate, gepirone, ghrelin, gimatecan, g-interferon, glatiramer acetate, gliatak, gliclazide, glimepiride, glimepiride, glipizide, glipizide; mefformin, glucagon, glucocorticoids, glutathione, glyburide, glyburide;metformin, glyceryl trinitrate, glycine, glycopyrrolate, granulocyte macrophage colony-stimulating factor (gm-csf), ganglioside conjugated vaccines, for example, gmk by Progenics Pharmaceuticals, golimumab, gonadotropic, chorionic, gonadotropin-releasing hormone, goserelin acetate, gramicidin;neomycin;polymyxin b sulfate, granisetron, granisetron hydrochloride, griseofulvin, group c meningococcal conjugate vaccine, growth hormone, gti 2040 antisense agent, guaifenesin, guaifenesin; pseuodoephedrine, guanabenz acetate, guanfacine hydrochloride, guanidine hydrochloride, gusperimus trihydrochloride, gvak (leukemia, pancreatic, prostate), h. pylori urease breathe test, halcinonide, halobetasol propionate, halofuginone hydrobromide, haloperidol, haloperidol decanoate, haloperidol lactate, haloperidole, halothane, hydrochlorothiazide (hctz); olmesartan, quinipril, hctz;spironolactone, heliox, heparin sodium, hepatitis a & b vaccine, hepatitis a vaccine inactivated, hepatitis b immune globulin, hepatitis b vaccine, hepatitis c immunoglobulin, hepatocyte growth factor gene therapy, heptylpenicillin, herpes dna vaccine, herpes simplex virus, hetacillin, hexachlorocyclohexane, hexachlorophene, hexavalent vaccine, mapatumumab (hgs-etr1), hgs-etr2, hgs-tr2j, hgtv43 gene medicine, hib vaccine, hib; neisseria mening; hep b antigen vaccine, histamine dihydrochloride, histrelin, hiv dna vaccine, hiv recombinant vaccine, hla-b27 derived peptide, homatoprine methylbromide, homoharringtonine, homoharringtonine, hrecombinant atiii, h-tyrosine-glycine-phenylalanine-glycine-glycine-oh, huc242-dm4, human alpha1-proteinase inhibitor, human chorionic gonadotropin, human cytomegalovirus immunoglobulin, human hpv vaccine, human immunoglobulin, human interleukin-2, human liver cell therapy, human menopausal gonadotropin, human monoclonal antibody, human monoclonal antibody ab88bv59, human monoclonal antibody against hla-dr, human monoclonal hepatitis b immunoglobulins, human normal immunoglobulin (ivig, human placental lactogen, human *staphylococcus aureus* immunoglobulin, human telomerase reverse transcriptase peptide, humanized agonistic anti-cd28 monoclonal antibody, ofatumumab, for example, HUMAX-CD20® (sold by Genmab A/S), zanolimumab, for example, HUMAX-CD4®(sold by Genmab A/S), humax-egfr, hun901-dml, fontolizumab, for example, HUZAF® (sold by PDL Biopharma, Inc), hyaluronidase, hydralazine hydrochloride, hydralazine; hctz, hydralazine; hydrochlorothiazide, hydralazine; isdn, hydrazine, hydrocodone bitartrate, hydrocodone; acetaminophen hydrocodone; homatropine, hydrocodone; ibuprofen hydrocortisone, hydrocortisone sodium succinate, hydrocortisone valerate, hydrocortisone; neomycin; polymixin b, hydrocortisone; pramoxine, hydroflumethiazide, hydrogenated ergot alkaloids, hydromorphone, hydromorphone hydrochloride, hydroxocobalamin, hydroxyamphetamine; tropicamide, hydroxychloroquine sulfate, hydroxyethyl starch, hydroxypropyl cellulose, hydroxyurea, hydroxyzine, hydroxyzine hydrochloride, hydroxyzine pamoate, hyoscine, ibandronic acid, ibuprofen, pseudoephedrine, ibutilide fumarate, icatibant acetate, icodextrin, idarubicin hydrochloride, idazoxan, idebenone, idoxuridine, iduronate-2-sulfatase, idursulfase, ifosfamide, ign101, ign311, it 13-pe38qqr, il-lr, il-2, il-2/ep, il-21, il-4r, iloprost, ima-638, imatinib, imatinib mesilate, imatinib mesylate, imc-3g3/imc-11f8/imc-18f1/imc-1121b/imc-a12, imexon, imiglucerase, imipramine, imipramine hydrochloride, imiquimod, immu-100/immu-101/immu-102/immu-105/immu-106/immu-107, immune globulin, inactivated hepatitis a virus; hepatitis b surface antigen suspension, inactivated hepatitis b vaccine, inactivated polio virus vaccine, inactivated rabies virus vaccine, inamrinone lactate, indapamide, INDICLOR® (sold by GE Healthcare), indinavir, indium dtpa in 111, indium in 111 chloride, indium in 111 oxyquinoline, indium in 111 pentetate disodium, indium in 111 pentetreotide, indocyanine green, indomethacin, indomethacin sodium, indoprofen, infliximab, ing 1, ingap peptide, ingn 225/ingn 234/ingn 241/ingn 401, inhibin, inn-carglumic acid, inn-ivabradine, inno 102, inno-105/inno-305/inno-406, inn-protein c, inolimomab, ins37217 (P2Y(2) receptor), insulin (r dna origin), insulin (recombinant human), insulin aspart, insulin aspart recombinant, insulin detemir recombinant, insulin glargine recombinant, insulin glusine, insulin lispro protamine recombinant, insulin purified pork, insulin zinc, insulin-like growth factor, interferon alfa-2a, interferon alfason-1, interferon alpha, interferon b 1a, interferon beta 1-b, interferon beta gene delivery, interferon beta-1a, interferon gamma, interferon gamma-1b, interferon omega, interleukin-1 trap, interleukin-3/interleukin-12, intravenous immune globulin, iobenguane sulfate i 131, iodinated 125 albumin, iodinated 131 albumin, iodine iodipamide meglumine, iodixanol, iodo-1-phenylalanine, iohexol, iopamidol, iothalamate meglumine, iothalamate sodium, ioversol, ioxaglate meglumine, ioxaglate sodium, ipilimumab, ipratropium bromide, iproniazid, ipsapiraone, ir103 w/amplivax, irbesartan, irbesartan; hydrochlorothiazide (hctz), irbesartan; hydrochlorothiazide, irinotecan hydrochloride, iron dextran, iron sucrose, isf 154, isis 113715 (20-mer phosphorothioate antisense oligonucleotide), mipomersen (isis 301012), isocarboxazid, isoetharine hydrochloride, isoflurane, isoleucine, isometheptene, isoniazid, isophane insulin, isoproterenol, isoproterenol bitartrate, isoproterenol hydrochloride, isosorbide dinitrate, isosorbide mononitrate, isosulfan blue, isotonic gentamicin sulfate, isotretinoin, isradipine, itraconazole, iv fat emulsion, iv lipids, ivabradine, ivermectin, kanamycin, kanamycin sulfate, ketamine, ketamine hydrochloride, ketoconazole, ketoprofen, ketorolac, ketorolac tromethamine, ketotifen, kitanserin, kl-4 peptide+lipid, kos-862/kos-953 kp-1461, labetalol hydrochloride, lactated ringer's, lactoferin, lactulose, I-alphaacetylmethadol, lamivudine, lamivudine;zidovudine, lamotrigine, lanreotide, lansoprazole, lanthanum carbonate, laronidase, I-asparaginase, latanoprost, lazabemide, leflunomide, lenalidomide, lentiviral vector, lep-etu/lep-sn38, lepirudin recombinant, leptin, lerafaon-etu, lesopitron, lestaurtinib, letrozole, leucovorin calcium, leuprolide, leuprolide acetate, levalbuterol hydrochloride, levamisol hydrochloride, levetiracetam, levobunolol hydrochloride, levocabastine, levocarnitine, levodopa, levodopa and carbidopa, levodopa; carbodpa, levofloxacin, levonorgestrel, levorphan tartrate, levorphanol, levorphanol tartrate, levothyroxine sodium, liarozole, lidocaine, lidocaine hydrochloride, lidocaine; prilocaine, lidocaine;tetracaine, lignocaine; polymyxin b sulfate, lincomycin hydrochloride, linezolid, liothyronine sodium, liposomal doxorubicin, liposomal morphine, liraglutide, lisinopril, lisinopril;hctz, lisuride, lithium carbonate, lithium citrate, live, attenuated typhoid vaccine, I-lysine-n-acetyl-I-cysteinate, iodine, lodoxamide tromethamine, lofentanil, lofepramine, lomefloxacin hcl, lomustine, loperamide hydrochloride, lopinovir; ritonavir, loprazolam, loracarbef, loratidine, lorazepam, losartan; hctz, losartan; hydrochlorothiazide, loteprednol, loteprednol etabonate, lovastatin, lovastatin; niacin, loxaglate sodium, loxapine, loxapine succinate, loxilan, bimatoprost, for example, LUMIGAN® (sold by Allergan); timolol, lumiracoxib, lusupultide, luteinizing hormone, anti-survivin antisense oligonucleotide (ly 2181308), ly2275796, lymphostat-b, lysine acetate, m m r vax ii injection, m.t.e.-4/m.t.e-6, m195-bismuth 213 conjugate, m200, mab hefi-1 monoclonal antibody, mafenide acetate, tumor rejection antigen mage-3, magnesium chloride, magnesium sulfate, malathion, mangafodinir trisodium, manganese chloride, mannitol, mannitolum, maprotiline hydrochloride, maprotoline, mart-1 melanoma vaccine, matuzumab, mazipredone, Iratumumab (mdx-060; a fully humanized anti-CD30 immunoglobulin G1 kappa monoclonal antibody), mdx-066, mdx-070 a human anti-plasma antibody), mdx-1100 (a fully human anti-CXCL10 monoclonal antibody), Valortim (mdx-1303; a fully human monoclonal antibody with a high affinity for *Bacillus anthracis* protective antigen (PA)), mdx-214 (anti-EGFr/CD89 antibody), measles mumps rubella vaccine, measles mumps vaccine, mebendazole, mebrofenin, mecamylamine hcl, mecasermin, mecasermin recombinant, mecasermin rinfabate, mecasermin rinfabate recombinant, mechlorethamine hydrochloride, meclizine hydrochloride, meclofenamate, meclofenamate sodium, mecloqualone, medetomidine, medi-507 siplizumab, medi-522 (monoclonal antibody specific for alphavbeta3 integrin), medi-528 anti-il-9 mab (humanized mAB against IL-9), medi-534 rsv/piv-3 vaccine (medi-534 is a live vectored RSV vaccine comprising bovine parainfluenza virus type 3 (PIV3) genome with substituted human PIV3 F and HN glycoproteins engineered to express RSV F protein), medi-545 (a fully anti-IFN-alpha monoclonal antibody), medifoxamine, medroxyprogesterone acetate, mefenamic acid, mefloquine, mefloquine hydrochloride, megestrol acetate, melanocyte-stimulating hormone, melatonin, melonom tumor-reactive autologous til, meloxicam, melperone, melphalan hydrochloride, memantine, meningococcal group c vaccine, meningococcal polysaccharide vaccine, menotropins, menthol, mepenzolate, meperidine, meperidine hcl, meperidine hydrochloride, mepivacaine hydrochloride, mepivicaine; levonordefrin, mepolizumab, meprobamate, meptazinol, mequinol; tretinoin, mercaptamine bitartrate, mercaptopurine, meropenem, mesalamine, mesalamine; 5-asa, mesna, mesoridazine, metampicillin, metaproterenol, metaproterenol sulfate, metaraminol bitartrate, metastable technetium 99 demogastrin 2, metaxalone, metformin, metformin hydrochloride, pioglitazone, rosiglitazone, methacholine chloride, methadone hydrochloride, methamphetamine hcl, methaqualone, methazolamide, methenamine hippurate, methenamine mandelate, methicillin, methimazole, methocarbamol, methohexital sodium, methotrexate, methotrexate sodium, methotrimeprazine, methoxsalen, methprylon, methscopolamine, methsuximide, methyclothiazide, methyl aminolevukinate, methyldopa, methyidopa; hctz, methyldopate hydrochloride, methylene-tetrahydrofolate, methylene-tetrahydrofolic acid, methylergonovine maleate, methylphenidate, methylphenidate hydrochloride, methyl-phosphorothioate oligonucleotide, methylprednisolone, methylprednisolone acetate, methylprednisolone sodium succinate, methyltestosterone, methyphenidate, methyprylon, methysergide, metipranolol, metoclopramide, metoclopramide hydrochloride, metofenazate, metolazone, metomidate, metopimazine, metopon, metoprolol, metoprolol tartrate, metralindole, metronidazole, metronidazole; nystatin, metyrapone, metyrosine, mexiletine hydrochloride, mg98, mianserin, micafungin sodium, miconazole, micophenolic acid, micro+4/micro+5/micro+6/micro cr/micro cu/micro i/micro mn/micro se, midazolam, midazolam hydrochloride, midodrine hydrochloride, midostaurin, mifepristone, miglitol, miglustat, milnacipran, milrinone lactate, miltefosine, minaprine, minocycline, minocycline hydrochloride, minoxidil, mirtazapine, misoprostol, mitomycin, mitotane, mitoxantrone, mitoxantrone hydrochloride, mivacurium chloride, min 1202, min-02, mm-093, chicken pox vaccine, moclobemide, modafinil, moexipril hcl;hydrochlorothiazide, moexipril hydrochloride, mofegiline, molindone hcl, mometasone furoate, monobenzone, monoclonal antibody to human interleukin-6, monocyte-derived activated killer (mak) cells, montelukast sodium, morab 003, morab 009, moricizine, morphine, morphine sulfate, MOSQUIRIX® malaria vaccine (sold by GlaxoSmithKline), moxifloxacin hydrochloride, mpi dmsa kidney reagent, mpi dtpa kit—chelate, mpi indium dtpa in 111, multi-11/multi-12, multivitamin infusion, mumps vaccine, mupirocin, muramyl tripeptide phosphatidyl ethanolamine, murine anti-idiotypic antibody against oc125 antibody against ca125 antigen, murine monoclonal antibody mab ar 20.5, muromonab-cd3, m-vax, mycophenolate mofetil hydrochloride, myeloma-derived idiotypic antigen vaccine, yo-029, myristoylated-peptidyl-, nabilone, nabumetone, n-acetylgalactosamine-4-sulfatase, n-acetylsarcosyl-glycyl-I-valyl-d-allo-isoleucyl-I-threonyl-I-norvalyl-I-isoleucyl-I-arginyl-I-prolyl-n-ethylamide, nadolol, nadrolone decanoate, nadroparin, nafcillin, nafcillin sodium, naftifine, nalbuphine, nalbuphine hydrochloride, nalidixic acid, nalmefene, nalmefene hydrochloride, nalorphine, naloxone, naloxone hydrochloride, naltrexone, naltrexone hydrochloride, nandrolone decanoate, nanopeptide paclitaxel, naphazoline hydrochloride, naphazoline;antazoline, naphazoline;pheniramin, naproxen, naproxen sodium, naratriptan, natalizumab, natamycin, natarelin acetate, nateglinide, n-azaphenyl-aminothiopyrrole, nbi-5788 (Neurocrine Biosciences; an analog of an immunodominant epitope), nbi-6024 (altered peptide ligand corresponding to the 9-23 amino acid region of the insulin B chain), n-carbamyl-I-glutamic acid, nedocromil sodium, nefazodone, nefazodone hydrochloride, nefopam, nelarabine, nelfinavir, nemorubicin hydrochloride, neomycin neomycin sulfate, nepafenac, nesiritide recombinant, 131-Iodine, for example, NEURADIAB® (by Bradmer Pharmaceuticals, Inc), neuropeptide y, nevirapine, niacin, nicardipine hydrochloride, nicergoline, nicotine, nicotine polacrilex, nifedipine, nilotinib, nilutamide, nimoripine, nimotuzumab, nisoldipine, nisoxetine, nitazoxamide, nitisinone, nitisinone, nitrofurantoin, nitrofurazone, nitroglycerin, nitrous oxide, nitrous oxide;oxygen (50:50), nizatidine, nix p101, nm01, nofetumomab, nomifensine, noradrenaline, norepinephrine bitartrate, norethindrone, norethindrone acetate, norfloxacin, norgestrel; ethinyl estradiol, norlegestromin;ethinyl estradiol, nortriptyline, nortriptyline hydrochloride, nt501 ciliary neurotrophic factor, triamcinolone, obestatin, ocrelizumab, octreotide acetate, ofloxacin, curtirsen (ogx-011), okt3-gamma-1, olanzapine, oligonucleotide phosphorothioate, olopatadine hydrochloride, olsalazine sodium, omalizumab, omega 3 and ethyl esters, omeprazole, omoconazole, ondansetron, ondansetron hydrochloride, ondansetron hydrochloride dihydrate, ondansetron omega, opebacan, opium tincture, oprelvekin, oral cholera vaccine, oral recombinant human growth hormone, oral recombinant parathyroid hormone 1-34, oregovomab, orlistat, orphenadrine, orphenadrine citrate, orphendrine; aspirin;caffeine, oseltamivir phosphate, osteogenic protein-1 i, oxacillin sodium, oxaliplatin, oxalobacter formigenes strain he-1, oxandrolone, oxaprozin, oxazepam, oxcarbazepine, oxiconazole, oxo-pentanoic acid methyl ester, oxprenolol, oxtriphylline, oxybutynin chloride, oxybutynin nicobrand, oxycodone, oxycodone, oxycodone; acetaminophen, oxycodone; oxycodone; oxymetazoline, oxymethalone, oxymorphone hydrochloride, oxytetracycline, oxytocin, p501, p53 and ras vaccine, paclitaxel, palifermin, palivizumab, palonosetron, palonosetron hydrochloride, paloxitene hcl, pam 4, pamelteon, pamidronate disodium, pancreatic enzymes, pancuronium, pancuronium bromide, pantoprazole sodium, papaveretum, papaverine, papiprazole, paracoxib, paracoxib sodium, parathyroid hormone, parecoxib sodium, paricalcitol, paromomycin sulfate, paroxetine, paroxetine hydrochloride, paroxetine mesylate, PAXENE® (sold by Norton Healthcare, Ltd), pazopanib, pazopanib hydrochloride, pbl and til transduced with retroviral vector-expressing anti-gp100 tcr, pbl or til transduced with retroviral vector-expressing anti-mart-1 tcr gene, PEDIAZOLE® (by Abott Laboratories), pegademase bovine, pegaptanib sodium, pegaspargase, pegfilgrastim, peginterferon alfa-2a, peginterferon alpha 2b, pegvisomant, pegylated arginine deiminase, pemetrexed disodium, pemirolast, pemoline, penbutolol, penciclovir, penfluridol, penicillamine, penicillin, penicillin g, penicillin n, penicillin o, penicillin s, penicillin v, pentamidine isethionate, pentazocine, pentazocine hydrochloride, pentazocine lactate, pentazocine; acetaminophen, pentetate calcium trisodium, pentetate zinc trisodium, pentobarbital, pentobarbital sodium, pentosan polysulfate sodium, pentostatin, pentoxifylline, peptide 144 tgf-beta 1-inhibitor, peptides, perflutren, perflutren protein-type a microspheres, pergolide mesylate, pericyazine, perindopril, permethrin, perphenazine, dipyridamole, for example, PERSANTINE® (by Boehringer Ingelheim Pharmaceuticals), personalized anti-cancer vaccine, pethidine, pexelizumab, pg-cpt, phenazocine, phendimetrazine tartrate, phenelzine, phenobarbital, phenteramine, phentermine hydrochloride, phentolamine, phentolamine mesylate, phentytoin, phenyhydrazine, phenylephrine hydrochloride, phenytoin, phenytoin sodium, phosphodiesterase-5 inhibitor, phospholine iodide, php, php pyridoxalated hemoglobin polyoxyethylene, physiologic saline solution, pilocarpine, pilocarpine hydrochloride, pimecrolimus, pimozide, pindolol, pioglitazone, pipamerone, piperacetazine, piperacillin, piperacillin sodium, piperacillin sodium/tazobactam sodium, pipotiazine, pirbuterol acetate, pirbuterolnaloxone, pirfenidone, piroxicam, pirprofen, pizotifen, plicamycin, pneumococcal vaccine polyvalent, brostallicin (pnu-166196 a new minor groove DNA binder), podofilox, polyeptides, polyethylene glycol, polyhematoporphyrin, polymyxin b sulfate, polypeptide yy, polysaccharide diphtheria toxoid conjugate vaccine, polythiazide, poractant alpha, porfimer sodium, posaconazole, potassium acetate, potassium chloride, potassium citrate, potassium iodide, povidone iodine, ppy 3-36, pralidoxime chloride, pramipexole, pramlintide acetate, pramoxine; hydrocortisone, prasterone, pravastatin, praziquantel, prazosin, prazosin; polythiazide, prednicarbate, prednisolone, prednisolone acetate, prednisolone sodium phosphate, prednisolone;gentamicin, prednisone, pregabalin, prentoxapylline, prilocaine, primaquine, primidone, pro 140 (viral-entry inhibitor, CytoDyn Inc.), probenecid, probucol, procainamide hydrochloride, procaine, procaine hydrochloride, procarbazine, procaterol hcl, prochlorperazine, prochlorperazine edisylate, prochlorperazine maleate, procyclidine, progesterone, prolactin, prolifeprosan 20; carmustine, promazine, promethazine, promethazine hydrochloride, propacetamol, propafenone hydrochloride, propanedisulfonic acid, disodium salt, propanolol, propantheline bromide, proparacaine hydrochloride, propentofylline, propofol, propoxyphene, propoxyphene; propranolol, propranolol hydrochloride, propylpiperidine x hcl, propylthiouracil, finasteride, for example, PROSCAR® (sold by Merck & Co.), proscillaridin;verapamil, prosol, prostcyclin, protamine sulfate, proteinase 3 peptide vaccine, proteins, protriptyline, methacholine chloride, for example, PROVOCHOLINE® (sold by Methapharm, Inc.), prussian blue, psa: 154-163, pseudoephedrine hydrochloride, pseudomonas exotoxin-interleukin 13 chimeric protein, pseudophedrine;triprolidine, psma, parathyroid hormone (pth 1-34), pulmonary surfactant, purified bromelain, purified inactivated japanese encephalitis sa14-4-2 virus vaccine, pyrazinamide, pyrethrin;piperinyl butoxide, pyridostigmine bromide, pyridoxine hydrochloride, pyrimethamine, quadravalent hpv vaccine, quazepam, quetiapine, quinapril, quinapril hydrochloride, quinapril;hctz, quinidine gluconate, quinidine sulfate, quinine, r1550, r744 cera (red blood stimulator), rabaprazole, rabies immune globulin, radiotheracim, raloxifene, ramipril, ramoplanin, ranibizumab, ranitidine, ranitidine hydrochloride, ranpirnase, rasagiline, rasburicase, rav 12 monoclonal antibody, rdna hepatitis b vaccine, reboxetine, recombinant antibody derivative, recombinant dog gastric lipase, recombinant fusion protein, recombinant glycoprotein gp350 of epstein-barr virus, recombinant hepatitis b vaccine, recombinant histidine-tagged idiotype immunoglobulin fab fragment of clonal b-cell receptors, recombinant human acid alpha-glucosidase, recombinant human acid sphingomyelinase, recombinant human alpha-1-antitrypsin, recombinant human alpha-mannosidase, recombinant human arylsulfatase a, recombinant human bile salt-stimulated lipase, recombinant human c1-inhibitor, recombinant human factor xiii, recombinant human glucagon-like peptide, recombinant human insulin-like growth factor-i/recombinant human insulin-like growth factor binding protein-3, recombinant human interleukin-21, recombinant human monoclonal antibody to hsp90, recombinant human porphobilinogen deaminase, recombinant inhibitor of human plasma kallikrein, recombinant megakaryopoeisis-stimulating protein, recombinant methionyl human stem cell factor, recombinant microbial lipase, recombinant modified vaccinia virus ankara expressing tuberculosis antigen 85a, recombinant neuraminidase, recombinant p-selectin glycoprotein immunoglobulin, recombinant triple antigen hepatitis b vaccine, remacemide, remifentanil, remifentanil hydrochloride, remoxipride, remune hiv-1 immunogen, renal tumor-reactive autologous til and pbl, repaglinide, repertaxin I-lysine salt, rescinnamine, reserpine, resonium calcium, resten-mp, antisense oligonucleotides for treating cardiovascular restenosis, for example, RESTEN-NG® (by AVI BioPharma, Inc.), reteplase, retinol, retinol binding protein 4, retroviral gamma-c cdna containing vector, rfx111, recombinant human bmp-2 (rhbmp-2), rhcc10 (recombinant version of natural human CC10 protein), recombinant human insulin-like growth factor binding protein-3 (rhlgfbp-3), recombinant human mannos binding lectin (rhmbl), rho(d) immune globulin, rhthrombin, ribavirin, rifabutin, rifampicin, rifampin, rifampin;isoniazid, rifampin; pyrazinamide; isoniazid, rifapentine, rifaximin, riluzole, rimantadine hydrochloride, rimexolone, rimonabant, ringer's, risperidone, ritanserin, ritodrine, ritodrine hydrochloride, ritonavir, rituximab, rivastigmine, rivastigmine tartrate, rizatriptan, rn1219, tanezumab (rn624), rocuronium bromide, ropinirole hcl, ropivacaine, roseglitazone, rosiglitazone, rosiglitazone; glimepiride, rosuvastatin, rotigotine, roxindole, recombinant protective antigen 102 (rpa102), retinal pigment epithelium (rpe) cells with microcarriers, rubella virus vaccine live, rubidium chloride rb-82, rubitecan, rufinamide, rx 0201, s. pneumoniae recombinant vaccine, sabarubicin, sacrosidase, s-adenosylmethionine, salbutamol, salicylate, salmeterol xinafoate, salmetrol, samarium sm 153 lexidronam pentasodium, samarium sm-153, sapropterin, saquinavir, sargramostim, sbil-2 transduced autologous til (tumor-infultrating lymphocyte), scopolamine, secobarbital sodium, secretin, secretin synthetic human, secretin synthetic porcine, sehcat, selegiline, selegiline hydrochloride, selenious acid, selenium sulfide, sermorelin acetate, cycloserine, for example, SEROMYCIN® (sold by Eli Lilly & Co.), serotonin, sertaconazole, sertindole, sertraline, sestamibi miraluma, sevelamer, sevoflurane, sfg, sgn-00101, SGN-CD33® (manufactured by Seattle Genetics. Inc.), dacetuzumab sgn-40, sibrotuzumab, sibutramine, sildenafil, sildenafil citrate, silver nitrate, SIMPLIRIX® (by GlaxoSmithKline), simvastatin, sinapultide, dipalmitoylphosphatidylcholine, palmitoyloleoylphosphatidylglycerol and palmitic acid, sincalide, siplizumab, sipuleucel-t, sirolimus, sitaxentan sodium, sitaxsentan, sipi, sodium acetate, sodium aminohippurate, sodium benzoate/sodium phenylacetate, sodium bicarbonatee, sodium butabarbital, sodium butyrate, sodium chloride, sodium chromate, sodium dichloroacetate, sodium edecrin, sodium eglinide, sodium ferric gluconate, sodium ferric gluconate complex, sodium fluoride, sodium gluconate, sodium iodide, sodium iodide i 131, sodium lactate, sodium nitroprusside, sodium oxybate, sodium p.a.s., sodium phenylbutyrate, sodium phosphate, sodium polystyrene sulfonate, sodium tetradecyl sulfate, sodium valproate, solifenacin, soluble yeast beta-1,3/1,6-glucan, somatostatin, somatropin, somatropin (r dna), somatropin recombinant, sorafenib, sorafenib tosylate, sorbitol, sotalol, sotalol hydrochloride, spc+lipid, spectinomycin hydrochloride, spiperone, spironolactone, sps: sodium polystyrene sulfonate, ssl(dsfv)-pe38 (immunotoxin consisting of the anti-mesothelin Fv linked to a truncated Pseudomonas exotoxin), ssd: silver sulfadiazine, stavudine, sterile diluent, sterile provocholine solution, sterile vancomycin hydrochloride, stiripentol, streptokinase, streptomycin sulfate, streptozocin, strontium chloride strontium-89 (sr-89), strontium ranelate, suberoylanilide hydroxamic acid, succimer, succinyicholine chloride, sucralfate, sufentanil, sufentanil citrate, sulconazole nitrate, sulfacetamide sodium, sulfacetamide; prednisone, sulfadiazine, sulfadoxine;pyrimthamine, sulfamethoprim, sulfamethoxazole/trimethoprim, sulfasalazine, sulfentanil citrate, sulfinpyrazone, sulfisoxazole, sulindac, sulpiride, sumatriptan, sumatriptan succinate, sumitizib maleate, atacicept (taci-Ig), tacrine, tacrolimus, tacrolimus hydrate, tadalafil, talc, tamoxifen citrate, tamsulosin hcl, tandospirone, TAUFERON® (Pep en Corp.), tazarotene, t-cell replacement therapy, technetium 99 monoclonal antibody, technetium fanolesomab, technetium tc 99m, technetium tc 99m tsc, technetium tc-99 generator, technetium tc-99m albumin, technetium tc-99m apcitide, technetium tc-99m bicisate, technetium tc-99m depreotide, technetium tc-99m disofenin, technetium tc-99m exametazime, technetium tc-99m gluceptate, technetium tc-99m mebrofenin, technetium tc-99m medronate, technetium tc-99m mertiatide, technetium tc-99m oxidronate, technetium tc-99m pentetate, technetium tc-99m pyrophosphate, technetium tc-99m red blood cell, technetium tc-99m sestamibi, technetium tc-99m succimer, technetium tc-99m sulfur colloid, technetium tc-99m tetrofosmin, teduglutide, tegaserod maleate, teicoplanin, telbivudine, telithromycin, telmisartan, hydrochlorothiazide (hctz), telmisartan; hydrochlorothiazide, temazepam, temocillin sodium, temozolomide, temsirolimus, tenecteplase, teniparatide, teniposide, tenofovir, tenofovir; emtricitabine, terazosin hydrochloride, terbinafine, terbutaline, terbutaline sulfate, terconazole, terguride, teriparatide recombinant human, testalactone, testosterone, testosterone cypionate, testosterone enanthate, testosterone propionate, testosteroneacetate, testosteroneenanthate, testosteroneproprionate, tetanus and diphtheria toxoid, tetanus and diphtheria toxoids adsorbed, tetanus immune globulin, tetanus toxoid, reduced diphtheria toxoid and acellular pertussis vaccine, tetraazacyclotetradecane, tetracycline hydrochloride, tetracycline; metronidazole;bismuth subsalicylate, tetrahydrobiopterin, tetrahydrocannabinol, tetrahydrozoline, tetrahydrozoline hcl, tg 1042 (adenovirus-mediated IFNgamma gene delivery for the intratumoral therapy of primary cutaneous lymphomas, Transgene SA), tg 4001, tg 4010 (modified vaccinia Ankara expressing MUC1 and interleukin 2), tgaac94 (human tumor necrosis factor-immunoglobulin (IgG1) Fc fusion (TNFR:Fc) gene), tgaav-cf (an adeno-associated cystic fibrosis transmembrane conductance regulator (CFTR) viral vector/gene construct), transforming growth factor (tgf)-β2 specific phosphorothioate antisense oligodeoxynucleotide, thalidomide, thallium chloride, thallous chloride, thallous chloride t1-201, thc;cbp, theophylline, thiabendazole, thiamine hydrochloride, thiethylperazine, thioguanine, thioridazine, thioridazine hydrochloride, THIOTEPA® (Adienne Pharma & Biotech), thiothixene, thiothixene hydrochloride, thrombin (human), thrombopoietin, thromboxane, thymalfasin, thyroid-stimulating hormone, thyrotropin tissue stimulating hormone (tsh), thyrotropin alfa, thyrotropin-releasing hormone, thyroxine, tiagabine, tianeptine, tiaprofenic acid, ticarcillin disodium, ticilimumab, ticlopidine hydrochloride, tifacogin, tigecycline, tilarginine acetate, tiludronate disodium, timolol, timolol maleate, tinidazole, tioconazole, tiopronin, tiotropium bromide monohydrate, tipifarnib, tipranavir, tirofiban hydrochloride, tissue repair cells, titanium dioxide and bisoctrizole, tizanidine, tizanidine hydrochloride, tumor necrosis factor (tnf alpha 1a), ibalizumab (non-immunosuppressive monoclonal antibody that binds CD4 (tnx-355)), lebrikizumab (humanized monoclonal antibody (tnx-650)), tnx-832 (Sunol cH36), tobramycin, tobramycin sulfate, tobramycin; dexamethasone, tofenacin, tolazamide, tolbutamide, tolcapone, tolevamer, gt160-246 (high molecular weight soluble anionic polymer, toxin binding polymer), tolfenamate, tolfenamic acid, tolmetin sodium, tolterodine tartrate, topical vascular endothelial growth factor) vegf, topiramate, topotecan hydrochloride, toremifene citrate, torsemide, tositumomab, tp10 (soluble complement receptor 1), tpi-asm8 (dual modified phosphorothioate antisense oligonucleotides that down-regulate the expression of CC chemokine receeptor 3 and the common beta chains for the receptors for IL-3, IL-5 and GM-CSF), trabectedin, tradolapril; verapamil, trafermin, tramadol, tramadol;acetaminophen, trandolapril, tranexamic acid, tranylcypromine, trastuzumab, travoprost, travoprost;timolol, trazodone, trazodone hydrochloride, treosulfan, treprostinil, treprostinil sodium, tretinoin, triamcinolone acetonide, triamcinolone hexacetonide, triamterene, triamterene;hydrochlorothiazide, triazolam, tricarbocyanine, desonide, for example, TRIDESILON® (Park Laboratories, Inc.), trientine dihydrochloride, trientine hcl, triethylperazine, trifluoperazine, trifluoperazine hydrochloride, trifluperidol, triflupromazine, trifluridine, trihexyphenidyl, trihexyphenidyl hydrochloride, triiodothyronine, trimeprazine, trimethadione, trimethobenzamide, trimethobenzamide hydrochloride, trimethoprim, trimethoprim sulfate, trimethorprim sulfate; polymyxin b sulfate, trimetrexate glucuronate, trimipramine, triodothyronine, tripelennamine, triprolidine hydrochloride, triptorelin pamoate, troleandomycin, tromethamine, tropicamide, tropisetron, trospium chloride, troxacitabine, thioredoxin-1 (trx 1), thioredoxin-4 (trx 4), trypan blue, tryptophan, tuberculosis recombinant vaccine, tucotuzumab celmoleukin (fusion protein of a humanized monoclonal antibody and an interleukin-2), tumor necrosis factor, ty800 typhoid fever vaccine, TYKERB® (lapatinib, sold by Novartis), tyrosine, unoprostone, urea, urofollitropin, urokinase, ursodiol, urtoxazumab, valacyclovir, valdecoxib, valganciclovir, valleu-gin-glu-leu-asn-val-thr-val, valproate sodium, valproicacid, valrubicin, valsartan, vancomycin, vandetanib, vardenafil, varenicline, varicella zoster virus recombinant vaccine, vascular endothelial growth factor 2, vasoactive intestinal peptide, panitumumab, for example, VECTIBIX® (sold by Amgen), vecuronium bromide, vascular endothelial growth factor (vegf) trap, VEGLIN® (by Vasgene Therapeutics, Inc.), velafermin, veldon lozenges, venlafaxine, verapamil, verapamil hydrochloride, verteporfin, vigabatrin, viloxazine, vinblastine, vinblastine sulfate, vincristine sulfate, vinorelbine, vinorelbine tartrate, vectored immunoprohylaxis (vip), vitamin a acid, vitamin a palmitate, vitamin d, vitamin k, vitamin k1, voriconazole, vrc-hivadv 014-00-vp HIV vaccine (GenVec Inc., Gaithersburg, Md.), lentiviral HIV-based vector encoding anti-HIV antisense envelope sequences (vrx 496), von Willebrand factor vwf/fviii-concentrate, warfarin sodium, xaliproden hydrochloride, xenon, xtl 6865 (a combination of two fully human monoclonal antibodies (Ab68 and Ab65) against the hepatitis C virus E2 envelope protein), y-fowlpox, r-vaccinia-tricom vaccine (recombinant vaccinia-TRICOM vaccine), y-fowlpox-cea(6d) tricom vaccine (y-fowlpox-carcinoemryonic antigen (CEA), y-fowlpox-gm-csf vaccine (y-fowlpox-granulocyte-macrophage colony-stimulating factor vaccine), y-fowlpox-psa vaccine (y-fowlpox-prostate-specific antigen), yohimbine (alpha-blocker), yttrium (90y) antiferritin polyclonal antibodies, yttrium (90y) chloride, yttrium (90y) chloride, zafirlukast (synthetic, selective peptide leukotriene receptor agonist: 4-(5-cyclopentyloxy-carbonylamino-1-methyl-indol-3-ylmethyl)-3-methoxy-N-otolylsulfonylbenzamide), zalcitabine, zaledronic acid, zaleplon, zalospirone (selective 5-HT partial agonist of the azapirone chemical class), zanamivir (neuraminidase inhibitor), ziconotide (atypical analgesic agent), zidovudine (also known as azidothymidine (AZT) antiretroviral medication), zileuton (inhibitor of 5-lipoxygenase), zinc acetate, zinc acetate dehydrate, zinc acetate dihydrate, zinc chloride, ziprasidone, ziprasidone mesylate, zoledronic acid, zolmitriptan (selective 5-hydroxytryptamine1B/1D (5-HT1B/1D) receptor agonist), zolpidem, zonisamide, zopiclone, zoster vaccine, zosuquidar trihydrochloride, zotepine, zuclopenthixol, zyc 101a (a micro-encapsulated DNA vaccine encoding multiple HLA-A2-restricted E7-derived epitopes, ZYCOS, Inc. MGI Pharma), zyc 300 (anticancer immunotherapeutic agent; MGI Pharma Biologics, Eisai Co Ltd), and combinations thereof.

As noted above, any therapeutic agent can be encapsulated. In some embodiments, ii is desirable to encapsulate materials to promote the growth of the agent (for biological agents), promote the functionality of the agent after it is released from the encapsulation, or increase the agent's ability to survive or retain its efficacy during the encapsulation period. Materials known to promote cell growth include cell growth media, such as Dulbecco's Modified Eagle Medium (DMEM), fetal bovine serum (FBS), non-essential amino acids and antibiotics, and growth and morphogen factors such as basic fibroblast growth factor (bFGF), transforming growth factors (TGFs), Vascular endothelial growth factor (VEGF), insulin-like growth factor (IGF-I), bone morphogenetic growth factors (BMPs), nerve growth factors and related proteins.

Additional options for delivery via the silk-based drug delivery composition described herein can include DNA, siRNA, antisense, plasmids, liposomes and related systems for delivery of genetic materials; antibodies and antigen binding fragment thereof; peptides and proteins to active cellular signaling cascades; peptides and proteins to promote mineralization or related events from cells; adhesion peptides and proteins to improve gel-tissue interfaces; antimicrobial peptides; and proteins and related compounds.

In some embodiments, the therapeutic agent(s) for use in the present disclosure include, but are not limited to, those requiring relatively frequent dosing. For example, those used in the treatment of chronic disorders or conditions.

In some embodiments, the therapeutic agent is 2-[4-[3-[2-(trifluoromethyl)-10H-phenothiazin-10-yl]propyl]piperazin-1-yl]ethanol (fluphenazine) or 3,5-dimethyltricyclo [3.3.1.1$^{3,7}$]decan-1amine (3,5-dimethyladamantan-1-amine, memantine). Fluphenazine is presently available in oral and injectable dosage forms. Disadvantageously, fluphenazine has an incomplete oral bioavailability of 40% to 50% (due to extensive first pass metabolization in the liver) such that its half life is 15 to 30 hours. Memantine is presently available in oral dosage form as tablets, capsules or solution, under the brand Namenda by Forest Labs. In some embodiment, memantine can be administered in combination with one or more cholinesterase inhibitors (e.g., donepezil, razadyne and rivastigmin).

In some embodiments, the therapeutic agent is a cell, e.g. a biological cell. Cells amenable to be incorporated into the composition include, but are not limited to, stem cells (embryonic stem cells, mesenchymal stem cells, bone-marrow derived stem cells and hematopoietic stem cells), chrondrocytes progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., Science, 2007, 318, 1917-1920 and Takahashi K. et. al., Cell, 2007, 131, 1-12).

Cells useful for incorporation into the composition can come from any source, for example human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HU- VEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stem cells (mESC) mouse neural precursor cells, mouse pancreatic progenitor cells mouse mesenchymal cells and mouse endodermal cells.

In some embodiments, tissue culture cell lines can be used in the compositions described herein. Examples of cell lines include, but are not limited to, C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and Heath C. A., *Trends in Biotechnology*, 2000, 18, 17-19, content of both of which is herein incorporated by reference in its entirety.

Pharmaceutical Compositions and Administration

In yet another aspect, provided herein is method for sustained delivery in vivo of a therapeutic agent. The method comprising administering a silk-based drug delivery composition described herein to a subject. Without wishing to be bound by a theory, the therapeutic agent can be released in a therapeutically effective amount daily.

As used herein, the term "therapeutically effective amount" means an amount of the therapeutic agent which is effective to provide a desired outcome. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders.

Guidance regarding the efficacy and dosage which will deliver a therapeutically effective amount of a compound can be obtained from animal models of condition to be treated.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, GDF-8 binding assays, and immunological assays.

The dosage can be determined by a physician and adjusted, as necessary, to suit observed effects of the treatment. Generally, the therapeutic agents are administered so that the therapeutic agent is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody compounds, one preferred dosage is 0.1 mg/kg of body weight (generally 10 mg/kg to 20 mg/kg).

As disclosed herein, the silk-based drug delivery can provide a therapeutically effective amount of the therapeutic agent to a subject for a period of time which is similar to or longer than the period of time when the therapeutic agent is administered without the silk-based drug delivery composition. For example, amount of therapeutic agent released over a day provides a similar therapeutic effect as provided by the recommended daily dosage of the therapeutic agent when administered without the silk-based drug delivery composition.

For administration to a subject, the silk-based drug delivery composition can be formulated in pharmaceutically acceptable compositions which comprise a drug delivery composition, formulated together with one or more pharmaceutically acceptable carriers (additives) and/or diluents. The drug delivery composition can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery composition. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

As used herein, the term "administered" refers to the placement of a drug delivery composition into a subject by a method or route which results in at least partial localization of the pharmaceutically active agent at a desired site. A drug delivery composition described herein can be administered by any appropriate route which results in effective treatment in the subject, i.e. administration results in delivery to a desired location in the subject where at least a portion of the pharmaceutically active agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, a drug delivery composition described herein can be implanted in a subject. As used herein, the term "implanted," and grammatically related terms, refers to the positioning of the silk-based drug delivery composition in a particular locus in the subject, either temporarily, semi-permanently, or permanently. The term does not require a permanent fixation of the silk-based drug delivery composition in a particular position or location. Exemplary in vivo loci include, but are not limited to site of a wound, trauma or disease.

Method of Treatment

Without limitations, method of sustained delivery described herein can be used for administering, to a subject, a pharmaceutical agent that requires relatively frequent administration. For example, a pharmaceutically active agent that requires administration at least once every three months, at least once every two months, at least once every week, at least once daily for a period of time, for example over a period of at least one week, at least two weeks, at least three weeks, at least four weeks, at least one month, at least two months, at least three months, at least four months, at least five months, at least six months, at least one years, at least two years or longer.

As is known in the art, many therapeutic agents for treatment of chronic disorders or conditions require relatively frequent dosing. Thus, provided herein is method for treatment of a chronic disease or disorder in subject. The method comprises administering a a silk-based drug delivery composition described herein or a pharmaceutical composition comprising silk-based drug delivery composition described herein to subject in need thereof. The silk-based drug delivery comprises a therapeutic agent that requires frequent administration for treatment of chronic disease or condition under consideration.

Exemplary chronic diseases include, but are not limited to, autoimmune disease including autoimmune vasculitis, cartilage damage, CIDP, Cystic Fibrosis, diabetes (e.g., insulin diabetes), graft vs. host disease, Hemophilia, infection or other disease processes, inflammatory arthritis, inflammatory bowel disease, inflammatory conditions resulting from strain, inflammatory joint disease, Lupus, lupus, Multiple Sclerosis, Myasthenia Gravis, Myositis, orthopedic surgery, osteoarthritis, Parkinson's Disease, psioriatic arthritis, rheumatoid arthritis, Sickle Cell Anemia, sprain, transplant rejection, trauma, and the like.

By "treatment, prevention or amelioration" is meant delaying or preventing the onset of such a disorder or reversing, alleviating, ameliorating, inhibiting, slowing down or stopping the progression, aggravation or deterioration the progression or severity of such a condition. In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

In some embodiments, subject is need of treatment for schizophrenia or a bipolar disorder. The subject can be administered a silk-based drug delivery composition comprising 2-[4-[3-[2-(trifluoromethyl)-10H-phenothiazin-10-yl]propyl]piperazin-1-yl]ethanol (fluphenazine).

In some embodiments, subject is in need of treatment for Alzheimer's disease. The subject can be administered a silk-based drug delivery composition comprising 3,5-dimethyltricyclo[3.3.1.1$^{3,7}$]decan-1-amine (3,5-dimethyladamantan-1-amine, or memantine).

In some embodiments of the methods described herein further comprise selecting a subject diagnosed with or suspected of having a chronic disease or disorder. A subject suffering from a chronic disease or disorder can be selected based on the symptoms presented. For example, a subject diagnosed with or suspected of having schizophrenia, a bipolar disorder or Alzheimer's disease.

Embodiments of the invention can be described by any of the following paragraphs:

1. A silk-based drug delivery composition comprising a therapeutic agent encapsulated in a silk reservoir implant or silk injectable reservoir, wherein the silk reservoir implant or silk injectable reservoir comprises a silk fibroin matrix, wherein the silk fibroin matrix comprises a lumen extended therethrough and ends of the lumen are closed, wherein at least a portion of the therapeutic agent is present in the lumen, and wherein the composition is capable of sustained delivery of the therapeutic agent in vivo.
2. The silk-based drug delivery composition of paragraph 1, wherein the silk fibroin matrix is of a cylindrical shape.
3. The silk-based drug delivery composition of paragraph 1 or 2, wherein the silk fibroin matrix is a film-spun, gel-spun, or dip-coated tube.
4. The silk-based drug delivery composition of any of paragraphs 1-3, wherein the lumen has a cross-section diameter of has a diameter of about 100 nm to about 20 mm.
5. The silk-based drug delivery composition of any of paragraphs 1-4, wherein the silk fibroin matrix has a length of about 1 mm to about 10 cm.
6. The silk-based drug delivery composition of any of paragraphs 1-5, wherein the silk fibroin matrix has a wall thickness of from about 50 μm to about 5 mm around the lumen.
7. The silk-based drug delivery composition of any of paragraphs 1-6, wherein silk fibroin matrix comprises silk fibroin in an amount from about 1% to about 50% (w/v) of the silk fibroin matrix.
8. The silk-based drug delivery composition of any of paragraphs 1-7, wherein the silk solution used for fabricating the silk fibroin matrix comprises a therapeutic agent
9. The silk-based drug delivery composition of paragraph 8, wherein the therapeutic agent is same or different from the therapeutic agent in the lumen of the silk fibroin matrix.
10. The silk-based drug delivery composition of any of paragraphs 1-9, wherein the reservoir of the film-spun silk fibroin matrix contains a therapeutic agent
11. The silk-based drug delivery composition of any of paragraphs 1-10, wherein the therapeutic agent is further encapsulated in a silk sphere
12. The silk sphere of paragraph 11, wherein the silk sphere is a microsphere or nanosphere
13. The silk-based drug delivery composition of any of paragraphs 1-12, wherein the therapeutic agent is selected from the group consisting of small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.
14. The silk-based drug delivery composition of any of paragraphs 1-13, wherein the therapeutic agent is selected from the group consisting of a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides, and any combinations thereof.

15. The silk-based drug delivery composition of any of paragraphs 1-14, wherein the therapeutic agent is fluphenazine or memantine.

16. The silk-based drug delivery composition of any of paragraphs 1-15, wherein the therapeutic agent is present in an amount from about 0.001% (w/w) to about 95% (w/w) of the silk reservoir implant or silk injectable reservoir.

17. The silk-based drug delivery composition of any of paragraphs 1-16, wherein the composition comprises at least 1.25× recommended dosage of the therapeutic agent.

18. The silk-based drug delivery composition of any of paragraphs 1-17, wherein the composition comprises at less than half the recommended dosage of the therapeutic agent.

19. The silk-based drug delivery composition of any of paragraphs 1-18, wherein the composition releases the therapeutic agent at a rate of about 1 ng/day to about 1000 mg/day.

20. The silk-based drug delivery composition of any of paragraphs 1-19, wherein the composition releases the therapeutic agent at rate to provide a therapeutic effect substantially similar to the therapeutic effect provided by once daily dosage of the therapeutic agent.

21. The silk-based drug delivery composition of any of paragraphs 1-20, wherein the composition releases the therapeutic agent at near zero-order release kinetics over a period of at least one week.

22. The silk-based drug delivery composition of any of paragraphs 1-21, wherein the composition provides sustained delivery of the therapeutic agent over a period of at least one week.

23. The silk-based drug delivery composition of any of paragraphs 1-22, wherein the composition provides a duration of therapeutic effect that is at least one day longer than the duration of effect when the therapeutic agent is administered without the silk-based drug delivery composition.

24. The silk-based drug delivery composition of any of paragraphs 1-23, wherein the composition further comprises a targeting ligand.

25. The silk-based drug delivery composition of any of paragraphs 1-24, wherein the film-spun silk fibroin matrix has a silk II beta-sheet crystallinity content of at least about 5%.

26. The silk-based drug delivery composition of any of paragraphs 1-25, wherein in vivo half-life of a therapeutic agent is increased by at least 5% relative to the in vivo half-life of the therapeutic agent without the film-spun silk fibroin matrix.

27. A method comprising:
(i) forming a silk tube;
(ii) loading the silk tube with a therapeutic agent; and
(iii) closing ends of the silk tube, whereby the loaded therapeutic agent is retained in lumen of the silk tube.

28. The method of paragraph 27, wherein said closing the ends of the silk tube comprising clamping the tube ends and coating the clamped ends with silk.

29. The method of paragraph 27-28, wherein said forming the silk tube comprises gel-spinning, film-spinning, or dip-coating.

30. The method of any of paragraphs 27-29, wherein said forming of silk tube comprising:
(i) delivering, with an applicator, a silk solution onto a support structure, wherein the support structure is an elongated structure with a longitudinal axis, and wherein the support structure is reciprocated horizontally while being rotated along its longitudinal axis to form a silk coating thereon;
(ii) optionally heating the silk coating while the support structure is rotating; and
(iii) optionally repeating the delivering and heating steps to form one or more coatings of silk film thereon.

31. The method of paragraph 30, wherein the elongated structure is a stainless steel mandrel coated with a synthetic fluoropolymer.

32. The method of any of paragraphs 30-31, wherein the support structure has a rotational speed of about 0 to about 1000 rpm.

33. The method of any of paragraphs 30-32, wherein the support structure has an axial movement speed of about 0 to about 1000 mm/s.

34. The method of any of paragraphs 30-33, wherein the applicator is a syringe containing the supply of the silk solution.

35. The method of any of paragraphs 30-34, wherein the silk fibroin solution is delivered by a needle of at least 21 gauge.

36. The method of paragraph 35, wherein the needle is of gauge from about 21 to about 30.

37. The method of any of paragraphs 27-29, wherein said forming of silk tube comprising:
(i) dipping an elongated structure having a longitudinal axis with a silk solution, thereby forming a coating on the elongated structure;
(ii) drying the coating on the elongated structure; and
(iii) optionally repeating optionally repeating steps (i) and (ii) to form one or more coatings of silk film thereon.

38. The method of any of paragraphs 27-37, wherein the silk solution for forming the tube or for coating the clamped portions has a silk concentration of from about 1% to about 50% (w/v).

39. The method of any of paragraphs 27-38, wherein the silk tube has a lumen diameter of about 100 nm to about 10 mm.

40. The method of any of paragraphs 27-39, wherein the silk tube has a length of about 1 mm to about 10 cm.

41. The method of any of paragraphs 27-40, wherein said coating comprises dip-coating the silk tube.

42. The method of any of paragraphs 27-41, further comprising inducing a conformational change in the silk tube before loading the silk tube with the therapeutic agent.

43. The method of paragraph 42, wherein said inducing the conformation change comprising water annealing.

44. The method of paragraph 42, wherein said water annealing is at a temperature from about 4° C. to about 100° C.

45. The method of paragraph 42, wherein said inducing comprises treating the silk tube with an alcohol solution.

46. The method of paragraph 42, wherein the alcohol solution has an alcohol concentration of at least 10% (v/v).

47. The method of any of paragraphs 45 or 46, wherein the alcohol is methanol or ethanol.
48. The method of any of paragraphs 27-47, further comprising hydrating the silk tube before loading the silk tube with the therapeutic agent.
49. The method of any of paragraphs 27-48, further comprising drying the silk tube following the clamping thereof.
50. The method of any of paragraphs 27-49, wherein the silk solution used for making the silk tube or closing the ends of the silk tube comprises a therapeutic agent.
51. The method of paragraph 50, where the therapeutic agent is the same or different from the therapeutic agent retained in the lumen of the silk fibroin matrix.
52. The method of any of paragraphs 27-50, wherein the therapeutic agent retained in the lumen is further encapsulated in a silk sphere.
53. The method of paragraph 52, wherein the silk sphere is a microsphere or nanosphere.
54. The method of any of paragraphs 27-53, wherein the therapeutic agent is selected from the group consisting of small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.
55. The method of any of paragraphs 27-54, wherein the therapeutic agent is selected from the group consisting of a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides, and any combinations thereof.
56. The method of any of paragraphs 27-55, wherein the therapeutic agent is fluphenazine or memantine.
57. The method of paragraph 27, comprising:
   (i) forming a silk tube, wherein forming the silk tube comprises:
      a. delivering, a silk solution through a needle onto a wire which is concomitantly reciprocated horizontally while being rotated along its axis to form a silk coating thereon;
      b. optionally heating the silk coating, while rotating the wire, to form a silk film; and
      c. optionally repeating the delivering and heating steps to form one or more coatings of silk film thereon;
   (ii) optionally inducing a conformational change in the silk coating;
   (iii) optionally hydrating the silk tube;
   (iv) loading the silk tube with the therapeutic agent;
   (v) clamping the silk tube such that the therapeutic agent is sealed therein; and
   (vi) coating the clamped portions of the silk tube with a silk coating solution to form a silk reservoir implant or silk injectable reservoir.

58. The method of paragraph 27, comprising:
   (i) forming a silk tube, wherein forming the silk tube comprises:
      a. dipping an elongated structure having a longitudinal axis with a silk solution, thereby forming a coating on the elongated structure;
      b. drying the coating on the elongated structure; and
      c. optionally repeating optionally repeating steps (i) and (ii) to form one or more coatings of silk thereon
   (ii) optionally inducing a conformational change in the silk coating;
   (iii) optionally hydrating the silk tube;
   (iv) loading the silk tube with the therapeutic agent;
   (v) clamping the silk tube such that the therapeutic agent is sealed therein; and
   (vi) coating the clamped portions of the silk tube with a silk coating solution to form a silk reservoir implant or silk injectable reservoir.
59. The method of paragraph 57 or 58, wherein said inducing the conformation change comprising water annealing.
60. The method of paragraph 59, wherein said water annealing is at a temperature from about 4° C. to about 100° C.
61. The method of paragraph 59, wherein said inducing comprises treating the silk tube with an alcohol solution.
62. The method of paragraph 61, wherein the alcohol solution has an alcohol concentration of at least 10% (v/v).
63. The method of paragraph 61 or 62, wherein the alcohol is methanol or ethanol.
64. A silk-based drug delivery composition prepared according to any of paragraphs 27-58.
65. A method of preparing a silk fibroin cylindrical matrix, the method comprising:
   (i) delivering, with an applicator, a silk fibroin solution onto a support structure, wherein the support structure is an elongated structure with a longitudinal axis, and wherein the support structure is reciprocated horizontally while being rotated along its longitudinal axis to form a silk coating thereon;
   (ii) heating the silk coating while the support structure is rotating; and
   (iii) optionally repeating the delivering and heating steps to form one or more coatings of silk film thereon.
66. The method of paragraph 65, further comprising inducing a conformational change in the silk fibroin.
67. The method of paragraph 66, wherein said inducing the conformation change comprising water annealing.
68. The method of paragraph 67, wherein said water annealing is at a temperature from about 4° C. to about 100° C.
69. The method of paragraph 66, wherein said inducing comprises treating the silk tube with an alcohol solution.
70. The method of paragraph 69, wherein the alcohol solution has an alcohol concentration of at least 10% (v/v).
71. The method of paragraph 69 or 70, wherein the alcohol is methanol or ethanol.
72. The method of any of paragraphs 65-71, further comprising hydrating the silk fibroin cylindrical matrix.
73. The method of any of paragraphs 65-72, further comprising loading a therapeutic agent into the silk fibroin cylindrical matrix.
74. A pharmaceutical composition comprising the silk-based drug delivery composition of any of paragraphs 1-26 or 64 and a pharmaceutically acceptable excipient.
75. A kit comprising the silk-based drug delivery composition of any of paragraphs 1-26 or 64 and instructions for use.
76. A method of sustained delivery in vivo of a therapeutic agent comprising administering the composition of any of paragraphs 1-26 or 64 to a subject in need thereof.
77. A method for treating schizophrenia or a bipolar disorder in a subject, the method comprising administering a composition of any of paragraphs 1-26 or 64 to a subject in need thereof, wherein the therapeutic agent is fluphenazine.
78. A method for treating Alzheimer's disease in a subject, the method comprising administering a composition of any of paragraphs 1-26 or 64 to a subject in need thereof, wherein the therapeutic agent is memantine.

SOME SELECTED DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean ±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

"PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The term "tube" here refers to an elongated shaft with a lumen therein. The tube can typically be an elongate hollow cylinder, but may also be a hollow shaft of other cross-sectional shapes.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpinlike structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

The term "vaccines" as used herein refers to any preparation of killed microorganisms, live attenuated organisms, subunit antigens, toxoid antigens, conjugate antigens or other type of antigenic molecule that when introduced into a subjects body produces immunity to a specific disease by causing the activation of the immune system, antibody formation, and/or creating of a T-cell and/or B-cell response. Generally vaccines against microorganisms are directed toward at least part of a virus, bacteria, parasite, mycoplasma, or other infectious agent.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab')2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, N.Y., pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclines, lincosides, quinolones, chloramphenicol, vancomycin, metronidazole, rifampin, isoniazid, spectinomycin, trimethoprim, sulfamethoxazole, and the like.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

The term "immunogen" refers to any substance, e.g., vaccines, capable of eliciting an immune response in an organism. An "immunogen" is capable of inducing an immunological response against itself on administration to a subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T-cells that are directed towards the immunogen. A cellular immune response is elicited by the presentation of polypeptide epitopes in association with Class I or Class II MHC molecules to activate antigen-specific CD4+T helper cells and/or CD8+ cytotoxic T cells. Such a response can also involve activation of monocytes, macrophages, NK cells, basophils, dendritic cells, astrocytes, microglia cells, eosinophils or other components of innate immunity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Silk Memantine Reservoir Implants and Silk Fluphenazine Injectable Reservoirs

Materials and Methods

Degummed silk fibers were purchased from Suho Biomaterials Technology (Suzhou, China). Memantine hydrochloride and all other chemicals were purchased from Sigma-Aldrich (St. Louis, Mo.).

Regenerated Silk Solution:

Degummed silk fibers were dissolved in an aqueous LiBr solution (20 wt %) at 60° C. for 4 hours and dialyzed against deionized water for 2 days. The final degummed silk concentration varied between 5 to 8 wt %. Control batches of fibers were boiled in 0.02 M $NaCO_3$ for up to 300 min prior to dissolution in LiBr to reduce the average silk molecular weight and observe potential subsequent changes in tube swelling and degradation behavior. The reduction in silk average molecular weight due to the boiling treatment was determined via size exclusion chromatography (SEC, via an Agilent SEC-3 column) using an Agilent 1200 Series HPLC unit (Agilent Technologies, Santa Clara, Calif.) with UV detection at 280 nm. In SEC, increasing silk retention times indicate decreasing silk molecular weight. Possible changes in silk aqueous solution (5 wt %) viscosity due to the boiling treatment were investigated using a Viscolab 4000 viscometer (Cambridge Viscosity, Medford, Mass.).

Preparation of Concentrated Silk Solution:

Regenerated silk solution was concentrated to approx. 30 wt % via dialysis against 15 wt % aqueous, 10 kDa polyethylene glycol solution for 20 hours using 3 kDa MWCO Slide-A-Lyzer dialysis cassettes (Fisher Scientific). Silk concentration was estimated gravimetrically from the ratio of wet mass to dry mass.

Film Spinning:

Film spinning was conducted using the set-up depicted in FIG. 1. Briefly, a concentrated silk solution (30 wt %) was injected through a narrow gauge needle (≥21 G) onto a PTFE-coated stainless steel wire (McMaster-Carr). The silk solution flow rate was controlled (typical flow rates were 0.1 ml/min or 0.2 ml/min) using a KD Scientific syringe pump. During injection, the wire was concomitantly reciprocated horizontally (typically at 5 mm/min), while being rotated along its axis. The motion of the wire was controlled through an AC gear motor (McMaster-Carr) connected to another syringe pump (KD Scientific). For example, the solution flow rate was adjusted to dispense approx. 2 µL of 30% silk solution per millimeter of axial displacement of a 2.7 mm diameter wire rotating at 70 rpm. Immediately after injection of the silk solution onto the wire, the rotating wire was pushed into a tube oven to heat treat the silk coating thereby forming a silk film. The heat treatment temperatures were generally between 45° C. and 80° C. with a temperature variation of less than 0.08° C./mm along the film length. Simultaneous rotation of the wire during the heat treatment enhanced thickness uniformity of the silk film. The injecting/heating steps were repeated until the desired tube diameter was achieved. Optionally, silk tubes were soaked in 90:10 (vol/vol) methanol:water to induce silk II, beta-sheet crystallinity and subsequently incubated in deionized water until complete film hydration. The resultant silk tubes were removed from the wire and cut to a desired length.

Preparation of Silk Reservoir Implants or Injectable Silk Reservoirs:

Therapeutic agent was loaded in solution, powder or pellet form in silk-film tubes prepared as described above, while one end of the hydrated silk tube may be clamped. Following loading of therapeutic agent, the film-spun silk tube was clamped at the other end and allowed to dry at a suitable temperature (e.g., 20° C. or higher temperatures) for a suitable duration to allow complete drying of the tube and the loaded drug (e.g. overnight or longer). Drying conditions were selected to maximize stability of the therapeutic agent. Silk reservoir implants or injectable silk reservoirs were formed by clamping both ends of the silk tube and their subsequent coating (e.g., by dip-coating the ends) using a silk solution having a silk concentration of 30 wt % to ensure a tight seal and prevent dose dumping. The whole procedure was conducted aseptically inside a laminar flow hood.

In Vitro Release Assay:

The dosage forms were incubated in 250 mL PBS buffer containing 0.02 wt % sodium azide at 37° C. for up to 1 month. Release media was sampled after 2 and 6 hours and daily afterwards. After each sampling, the whole media was exchanged with fresh PBS (0.02 wt % sodium azide) buffer.

In Vivo Release Assay:

A 14-day rat pK study was conducted using silk memantine reservoir implants at a dose of 20 mg memantine/rat. Silk memantine reservoirs were implanted subcutaneously. Blood samples were collected serially at pre-determined time points for 14 days. Plasma samples were then analyzed for memantine concentration using liquid chromatography-tandem mass spectrometry (LC-MS/MS). Homogeneous silk memantine implants were used as a control group in a 3-day rat pK study. For homogeneous implant formulation, aqueous memantine solutions (up to 5 wt %) were mixed with concentrated silk solutions (approx. 30 wt %) inside conical PDMS molds and the mixture was dried at 60° C. In this manner, memantine was homogeneously encapsulated in silk implants.

Swelling Ratio:

Aqueous "equilibrium" swelling of silk films (S, %) was calculated using the formula:

$$S=(m_H-m_D)/m_D*100$$

where, $m_H$ and $m_D$ are hydrated and dry masses, respectively.

In Vitro Degradation:

In vitro degradation was measured gravimetrically at pre-determined time points for up to one week after incubation in PBS buffer containing 0.02 wt % sodium azide at 37° C.

Results and Discussion

Effects of Processing Conditions on Silk Tube Properties:

Effects of processing parameters, such as silk molecular weight, film drying temperature and film silk II, beta-sheet crystallinity as induced by methanol treatment on physicochemical properties, such as tube swelling or in vitro degradation were studied using control silk tubes (lacking therapeutic agent).

Figure 2:
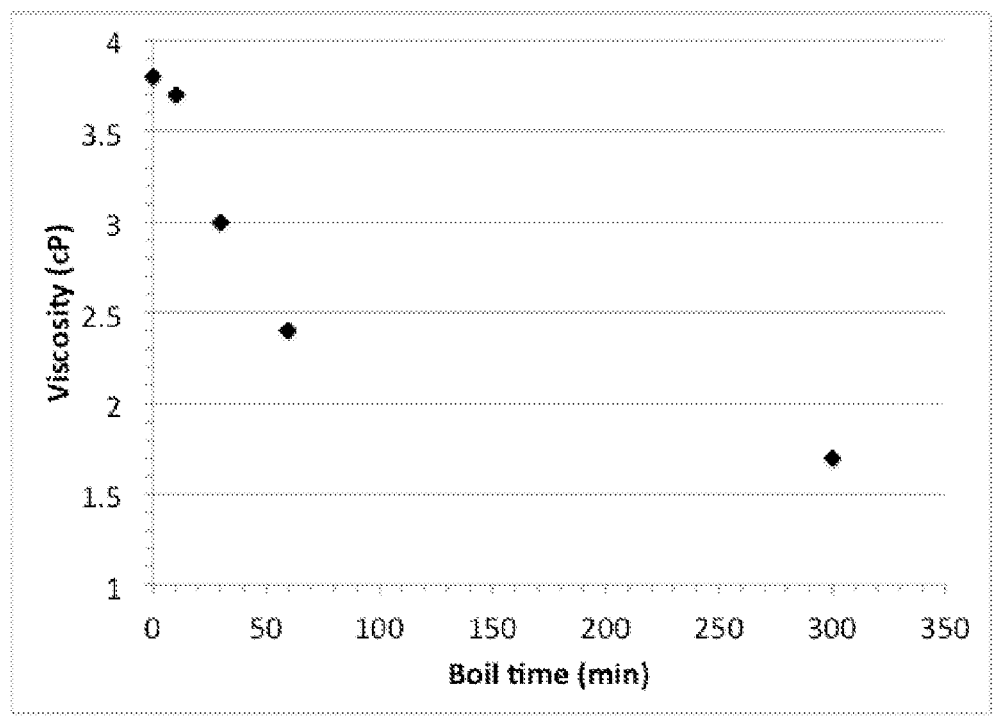
FIG. 2 illustrates changes in the viscosity of 5 wt % aqueous silk solution (lacking therapeutic agent) with increasing boiling time.

FIG. 2 highlights the decrease in silk solution viscosity with increasing boiling time, presumably due to decreasing silk molecular weight with increasing duration of the boiling treatment.

Figure 3A:
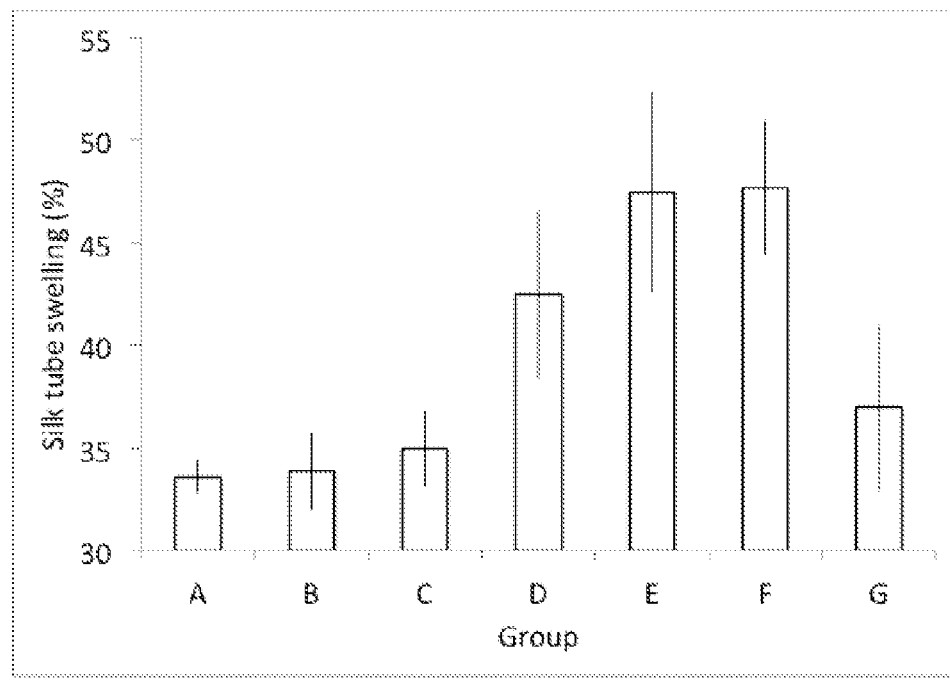
FIG. 3A is a bar graph illustrating percent aqueous swelling of film-spun silk tubes (lacking therapeutic agent) wherein tube processing was varied. Groups A and C were methanol treated after every 5 coats. The remaining groups (groups B, D-G) were not methanol treated. Different heat treatment conditions (temperature and duration) were applied to different groups after each coating step: The temperature and duration of the heat treatment were 67±3° C. for 5 min for groups A, B, E-G and 47±3° C. for 15 min for groups C and D. Note that error bars denote standard deviation from the mean values (n=3).

The aqueous "equilibrium" swelling of silk tubes (S, %) was calculated using the following equation:

$$S=(m_H-D)/m_D*100$$

where, $m_H$ and $m_D$ are hydrated and dry masses, respectively. Notably, the swelling ratio increased with decreasing molecular weight from 34% for non-boiled silk to 48% for 60 min boiled silk and dropped back to 37% for 300 min boiled silk (see FIG. 3A). Methanol treatment did not have a significant effect on swelling ratio in silk tubes heat treated at 67±3° C. (see FIG. 3A, Groups A and B). On the other hand, methanol treatment led to a lower swelling ratio when the silk tubes were annealed at 47±3° C. (see FIG. 3A, Groups C and D). This effect could be attributed to possible silk II crystal formation at high temperatures (e.g., 67±3° C.) even in the absence of methanol treatment.

Figure 3B:
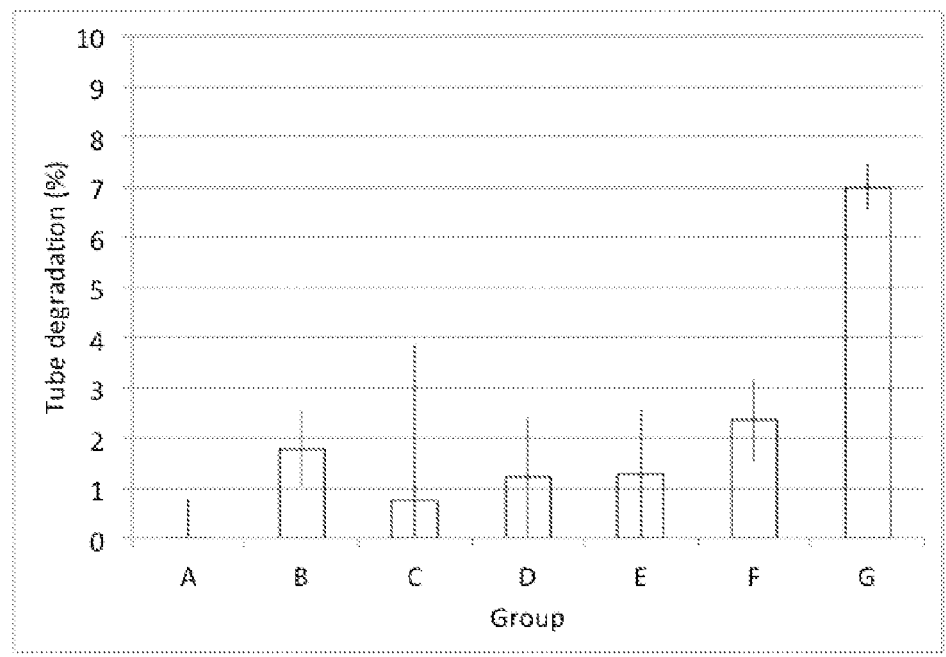
FIG. 3B is a graph that illustrates percent degradation of film-spun silk tubes (lacking therapeutic agent) in PBS following a one-week incubation period for Groups A-G as described above.

In Vitro Degradation:

Further, in vitro degradation was measured gravimetrically at pre-determined time points for up to one week after incubation in PBS buffer containing 0.02 wt % sodium azide at 37° C. Preliminary one-week data suggests that silk molecular weight may have a strong effect on initial tube degradation in vitro. Percent degradation values for non-methanol treated tubes prepared from 0, 10, 60 and 300 min boiled silk were 1.8%, 1.3%, 2.3% and 7%, respectively (FIG. 3B).

Silk Memantine Reservoir Implants:

An FDA approved therapeutic agent for Alzheimer's disease, memantine, was used as a model therapeutic agent to demonstrate sustained release from silk reservoir implant compositions. Silk reservoir implant compositions prepared as described above having either 2 or 10 coatings of silk film were loaded with 2.5, 5.0 or 10.0 mg memantine. These silk reservoir implant compositions were incubated in 250 mL PBS buffer containing 0.02 wt % sodium azide at 37° C. for up to 1 month. Release media was sampled after 2 hours, 6 hours and daily afterwards. After each sampling, the whole media was exchanged with fresh PBS (0.02 wt % sodium azide) buffer.

Figure 4:
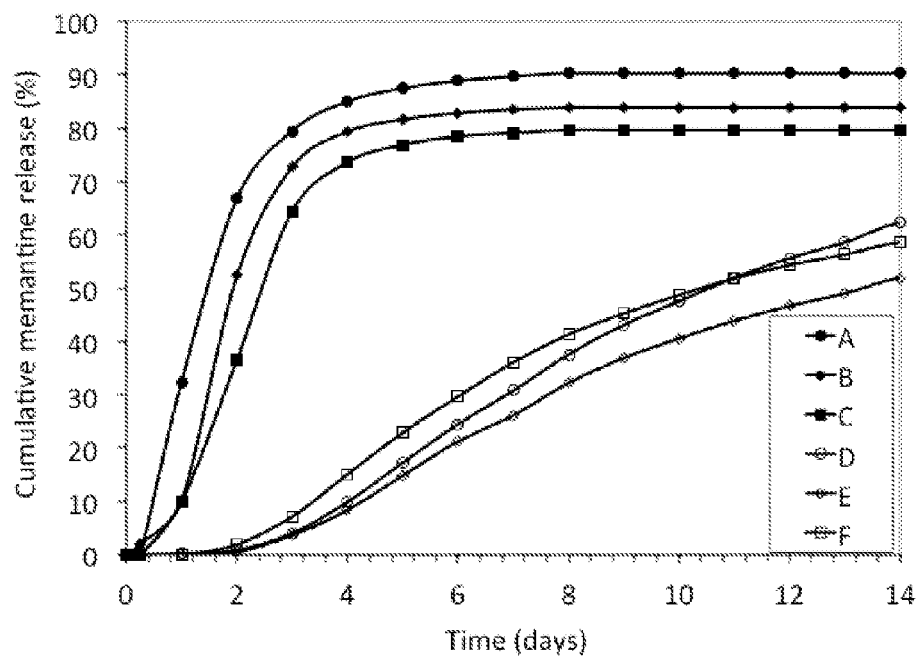
FIG. 4 is a graph that illustrates in vitro percentage cumulative release of memantine over time following incubation of silk reservoir implant compositions containing 2.5 mg, 5.0 mg, or 10.0 mg memantine and having wall thicknesses of 0.5 mm or 1.7 mm in PBS. The silk implant wall thickness for samples A, B and C was 0.5 mm, while memantine loading values were 2.5 mg, 5.0 mg and 10.0 mg, respectively. The silk implant wall thickness for samples D, E and F was 1.7 mm, while memantine loading values were 2.5 mg, 5.0 mg and 10.0 mg, respectively

Memantine release rate was strongly dependent on film thickness of the silk reservoir implant compositions. The daily release rates of memantine were 38%, 21% and 8% for 0.5, 1.0 and 1.7 mm thick silk films, respectively (see FIG. 4). On the other hand, there was no apparent effect of memantine dose when varied from 2.5 to 10 mg on the release rate (see FIG. 4). Importantly, no initial burst of memantine release was detected from these silk compositions. Furthermore, near zero-order release kinetics was achieved over 2 weeks in vitro at a release rate between 0.5 to 1.5 mg/day when the loading was normalized to 20 mg memantine per silk implant.

Silk reservoir implant compositions loaded with 20 mg memantine were implanted subcutaneously in rats and blood samples collected serially at pre-determined time points for 14 days. Plasma samples were then analyzed for memantine concentration using liquid chromatography-tandem mass spectrometry (LC-MS/MS). Additionally, for comparison, homogeneous silk memantine implants were used as a control group in a 3-day rat pharmacokinetic study. For homogeneous implant formulation, aqueous memantine solutions (up to 5 wt %) were mixed with concentrated silk solutions (approximately 30 wt %) inside conical polydimethylsiloxane molds and the mixture was dried at 60° C. In this manner, memantine was homogeneously encapsulated in silk implants.

Figure 5:
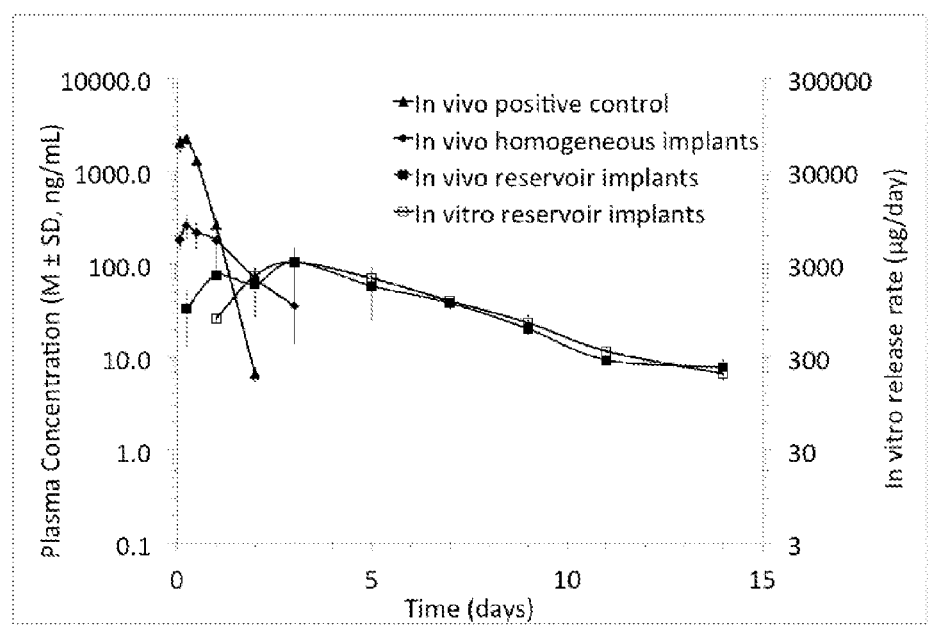
FIG. 5 is a composite graph that shows a comparison of the time evolution of in vitro and in vivo memantine release from silk reservoir implants with in vivo memantine release from a silk composition that homogeneously encapsulated memantine (homogeneous implant) and in vivo release from a single injection of memantine saline solution (positive control). In vivo data denote plasma memantine concentration (ng/mL) after administration of 20 mg memantine in rats subcutaneously. In vitro release rate of memantine from silk reservoir implant composition loaded with 20 mg memantine was reported in µg/day.

Silk reservoir implant compositions delivered memantine in a sustained manner over a period of 14 days (see FIG. 5). In contrast, memantine release from a single injection of memantine saline solution (terminal half life, $t_{1/2} \approx 4$ hours) or homogeneous silk memantine implants failed to deliver memantine in a sustained manner over a period of 14 days (see FIG. 5). Importantly, the silk compositions implanted into rats showed excellent biocompatibility as the incisions healed well and no adverse effects (e.g., inflammation, hardening or scar tissue formation) were noted throughout the study or during explanation. Moreover, a strong in vitro in vivo correlation (IVIVC) was observed with 1 mg/day (in vitro)≈33 ng/mL (rat plasma).

Silk Fluphenazine Injectable Reservoirs:

An FDA approved therapeutic for the treatment of Schizophrenia and acute manic phases of bipolar disorder, fluphenazine, was used as a model therapeutic agent to demonstrate sustained release from silk injectable reservoir compositions. Silk injectable reservoir compositions prepared as described above having dimensions 2 mm×18 mm (diameter×length) with a 0.5 mm silk film thickness were loaded with 3 or 10 mg fluphenazine. These silk injectable reservoir compositions were incubated in 250 mL PBS buffer containing 0.02 wt % sodium azide at 37° C. for up to 1 month. Release media was sampled after 2 hours, 6 hours and daily afterwards. After each sampling, the whole media was exchanged with fresh PBS (0.02 wt % sodium azide) buffer.

Figure 6:
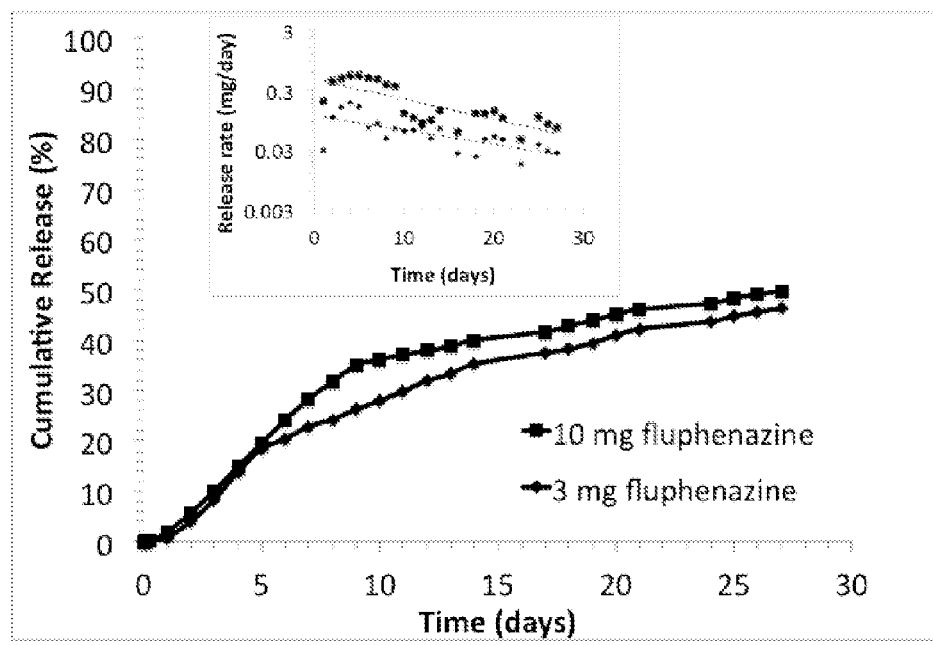
FIG. 6 is a graph that illustrates in vitro percentage cumulative release and in vitro release rate of fluphenazine from silk injectable reservoir compositions containing of 3 mg or 10 mg fluphenazine and having a wall thickness of 0.5 mm over time in PBS.
Figure 7:
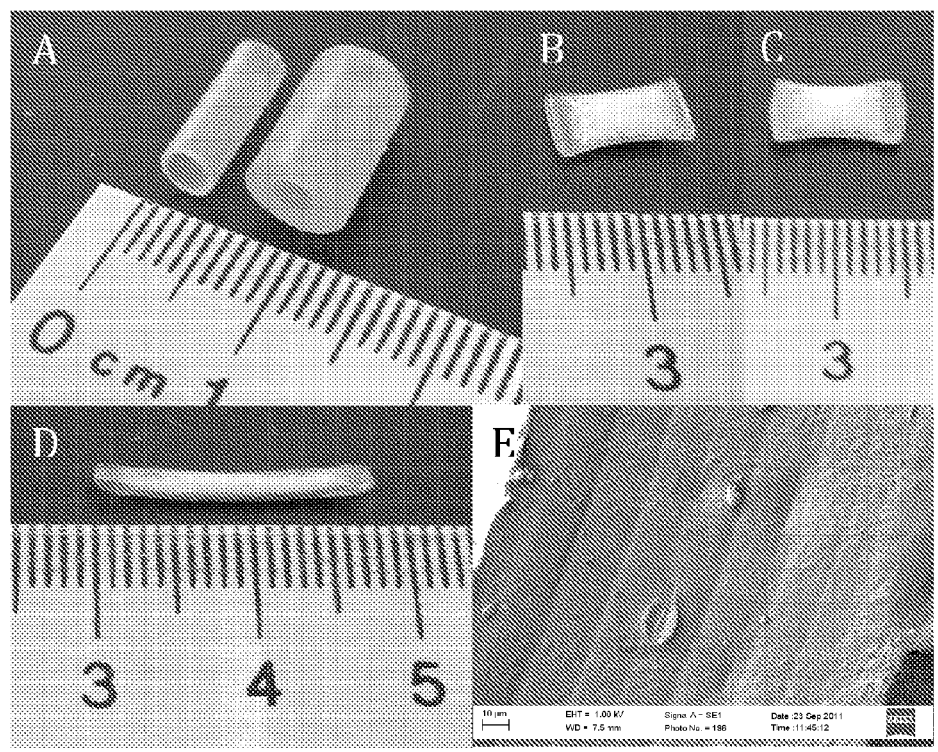
FIG. 7 Pictures of (A) film-spun silk tubes (ID×OD×L=2.5 mm×3.5 mm×10 mm or 2.5 mm×5.9 mm×10 mm), (B) a silk tube after drug loading and clamping, (C) a silk-drug reservoir implant, (D) an injectable silk-drug reservoir (ID×OD×L=1.5 mm×2.0 mm×18 mm). (E) SEM cross-sectional micrograph of a film-spun silk tube showing multiple layers of uniform silk coating.

The silk injectable reservoir compositions exhibited near zero-order release kinetics of fluphenazine for up to 1 month. Importantly, no initial burst of fluphenazine release was detected from these silk compositions. Furthermore, the release rate of fluphenazine varied between 0.05-0.5 mg/day and 0.02-0.2 mg/day for 3 and 10 mg fluphenazine loading, respectively, over a period of 25 days (see FIG. 6).

Example 2

Comparison of In Vitro Release with Prior Silk Memantine Formulations

In vitro release results obtained from various other silk compositions containing memantine demonstrated an undesirable high initial burst rather than sustained release of memantine.

Spheres:

Two different sphere formulations, namely PVA (polyvinyl alcohol) emulsion nanospheres and microspheres prepared using Spray-Crystallize-Freeze-Drying (SCFD) method (a provisional application for this method has been filed) were studied for memantine delivery. The mass ratio of silk to memantine was 4:1 and 2:1 in SCFD and PVA nanospheres, respectively. For PVA nanospheres, potential effects of two post sphere preparation methods (methanol treatment and incubation in silk and silk/memantine solutions) on memantine release were studied. However, in all cases high burst release values were observed, while the sustained release was below the target level of 50 μg/mL after 1 week.

Films:

Memantine release from silk films was investigated in a 96-well plate configuration. Films were prepared by drying silk/memantine solutions (2.5 wt % silk, 2.5% memantine) to obtain a homogeneous memantine encapsulation with or without additional coatings of silk film. Using different solution volumes (10-100 μL) varied the thickness of the silk/memantine films, while increasing the number of coatings from 1 to 4 using 5 wt % silk solution varied the thickness of the silk film. In the absence of additional coatings of silk film, the burst release was approximately 100%. Increasing the silk film thickness could reduce the burst release down to approximately 30%. However, linear release kinetics could not be achieved.

Coating:

Memantine pellets were prepared using either an Econo-Press purchased from Sigma Aldrich or a Table press purchased from Fisher Scientific. The pellets were drop coated with 100 μL of 8 wt % silk solution on both sides using a similar protocol to that described by Pritchard et al., *J Control Release*, 144(2):159-167 (2010) for adenosine-silk formulations. Possible effects of methanol treatment (after each coating step) on memantine release were also studied. In all cases, the release was predominantly due to a burst (≥90%).

Gels:

Three different gel formulations, silk hydrogels, lyophilized gels and air-dried gels, were prepared. For plain silk and air-dried gels, the initial silk concentration was varied between 8 and 30 wt % whereas lyophilized gels were only prepared from 8 wt % silk. In all cases, 5 mg memantine was added into 0.5 mL silk solution and the mixture was sonicated to obtain a hydrogel. Lyophilized gels showed the highest initial burst release (~85% after 6 hours), while lower burst values were observed for hydrogels and air-dried hydrogels. Increasing the silk concentration up to 29 wt % led to even lower initial burst values of approximately 20% after 6 hours. Although the sustained release values for hydrogels were higher as compared with that for the spheres, most of the encapsulated memantine (≥85%) was released after 2 weeks even at the highest hydrogel concentration.

Solids:

Silk/memantine solutions (5 mg memantine loading in 0.5 mL, 30% silk) were dried into solid plugs that are denser compared to the gels. The memantine loading in dried plugs could be improved 8-fold (40 mg memantine in 0.5 mL, 30% silk) by dissolution of memantine in methanol instead of water. There was a significant improvement in the release profile, a decrease in the burst and longer sustained release (approximately 75% of memantine release after two weeks) as compared with the hydrogels. However, the deviation was higher between repeats for plugs as compared to gels, possibly due to heterogeneous distribution of memantine in the matrix.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A silk-based drug delivery composition comprising a first therapeutic agent encapsulated in a silk reservoir implant or silk injectable reservoir, wherein the silk reservoir implant or silk injectable reservoir comprises a silk fibroin matrix, wherein the silk fibroin matrix comprises a lumen extended therethrough and ends of the lumen are closed, wherein at least a portion of the first therapeutic agent is present in the lumen, and wherein said composition provides a sustained delivery of the first therapeutic agent in vivo.

2. The silk-based drug delivery composition of claim 1, wherein the silk fibroin matrix is of a cylindrical shape.

3. The silk-based drug delivery composition of claim 1, wherein the silk fibroin matrix is a film-spun silk tube, gel-spun silk tube, or dip-coated silk tube.

4. The silk-based drug delivery composition of claim 1, wherein the silk reservoir implant or silk injectable reservoir comprising the silk fibroin matrix further comprises a second therapeutic agent that is the same or different from the first therapeutic agent.

5. The silk-based drug delivery composition of claim 1, wherein the first therapeutic agent is present in an amount from about 0.001% (w/w) to about 95% (w/w) of the silk reservoir implant or silk injectable reservoir.

6. The silk-based drug delivery composition of claim 1, wherein the composition comprises an amount of the first therapeutic agent that is at least 125% of the recommended dosage of said therapeutic agent.

7. The silk-based drug delivery composition of claim 1, wherein the composition comprises less than half of the recommended dosage of the first therapeutic agent.

8. The silk-based drug delivery composition of claim 1, wherein the composition releases the first therapeutic agent at a rate of about 1 ng/day to about 1000 mg/day.

9. The silk-based drug delivery composition of claim 1, wherein the composition releases the first therapeutic agent with no initial burst release.

10. The silk-based drug delivery composition of claim 1, wherein the composition provides sustained delivery of the first therapeutic agent over a period of at least one week.

11. The silk-based drug delivery composition of claim 1, wherein the first therapeutic agent provides a therapeutic effect for at least one day longer than the same amount of the first therapeutic agent administered without the silk-based drug delivery composition.

12. The silk-based drug delivery composition of claim 1, wherein the silk fibroin matrix has a silk II beta-sheet crystallinity content of at least about 5%.

13. The silk-based drug delivery composition of claim 1, wherein in vivo half-life of the first therapeutic agent is increased by at least 5% relative to the in vivo half-life of the first therapeutic agent administered without the silk-based drug delivery composition.

* * * * *